United States Patent
Rinderspacher et al.

(10) Patent No.: US 8,653,273 B2
(45) Date of Patent: Feb. 18, 2014

(54) POTENT NON-UREA INHIBITORS OF SOLUBLE EPOXIDE HYDROLASE

(75) Inventors: Kirsten Alison Rinderspacher, Bronx, NY (US); Donald W. Landry, New York, NY (US); Yuli Xie, New York, NY (US); Yidong Liu, New York, NY (US); Gangli Gong, Elmhurst, NY (US); Shi-Xian Deng, White Plains, NY (US)

(73) Assignee: The Trustees of Columbia University in the city of New York, New York, NY (US)

( * ) Notice: Subject to any disclaimer, the term of this patent is extended or adjusted under 35 U.S.C. 154(b) by 0 days.

(21) Appl. No.: 13/178,117

(22) Filed: Jul. 7, 2011

(65) Prior Publication Data

US 2012/0029022 A1 Feb. 2, 2012

Related U.S. Application Data

(63) Continuation of application No. PCT/US2009/057553, filed on Sep. 18, 2009.

(60) Provisional application No. 61/143,397, filed on Jan. 8, 2009.

(51) Int. Cl.
*C07D 211/62* (2006.01)

(52) U.S. Cl.
USPC ............................................ 546/225

(58) Field of Classification Search
None
See application file for complete search history.

(56) References Cited

U.S. PATENT DOCUMENTS

| | | | |
|---|---|---|---|
| 4,749,686 A | 6/1988 | Hintze | |
| 6,313,122 B1 * | 11/2001 | Beight et al. | 514/237.5 |
| 6,329,395 B1 * | 12/2001 | Dugar et al. | 514/329 |
| 6,531,506 B1 | 3/2003 | Kroetz et al. | |
| 2003/0139469 A1 | 7/2003 | Weiss et al. | |
| 2004/0110793 A1 | 6/2004 | Lloyd et al. | |
| 2006/0014792 A1 | 1/2006 | Lloyd et al. | |
| 2007/0207991 A1 | 9/2007 | Schwink et al. | |
| 2009/0163545 A1 * | 6/2009 | Goldfarb | 514/312 |

FOREIGN PATENT DOCUMENTS

| | | |
|---|---|---|
| WO | WO 2005037257 A2 * | 4/2005 |
| WO | WO 2007003934 A2 * | 1/2007 |
| WO | WO 2007118137 A1 * | 10/2007 |
| WO | WO 2010/080183 | 7/2010 |

OTHER PUBLICATIONS

Xie et al., Discovery of Potent Non-Urea Inhibitors of Soluble Epoxide Hydrolase, 19(8) Bioorg. Med. Chem. Letts. 2345-2359 (2008) (available online Sep. 20, 2008).*
Rautio et al., Prodrugs: Design and Clinical Applications, 7 Nat. Rev. Drug Dis., 255-70 (2008).*
International Search Report for PCT/US2009/057553 dated Nov. 17, 2009.
Imig, J.D. (2006) Cardiovascular therapeutic aspects of soluble epoxide hydrolase inhibitors. *Cardiovascular Drug Review*, 24(2) 169-188.
Larsen et al. (2007) Beyond vasodilation: non-vasomotor roles of epoxyeicosatrienoic acids in the cardiovascular system. *Trends in Pharmacological Sciences*, 28(1):32-38.
Sinal et al., (2000) Targeted disruption of soluble epoxide hydrolase reveals a role in blood pressure regulation. *Journal of Biological Chemistry*, 275(51):40504-40510.
Imig et al., (2002) Soluble epoxide hydrolase inhibition lowers arterial blood pressure in angiotensin II hypertension. *Hypertension*, 39(2 Pt 2):690-694.
Zhang et al., (2008) Soluble epoxide hydrolase gene deletion is protective against experimental cerebral. *Stroke*, 39(7): 2073-2078.
Yousif et al., (2007) Role of cytochrome P450 metabolites of arachidonic acid in regulation of corporal smooth muscle tone in diabetic and older rats. *Vascular Pharmacology*, 47(5-6): 281-287.
Jiang et al., Cytochrome p450 epoxygenase promotes human cancer metastasis. *Cancer Research*, 67(14): 6665-6674.
Ford et al., (2002) Prevalence of the metabolic syndrome among US adults: findings from the third National Health and Nutrition Examination Survey. *Journal of the American Medical Association*, 287(3): 356-359.
Kim et al., (2007) 1,3-disubstituted ureas functionalized with ether groups are potent inhibitors of the soluble epoxide hydrolase with improved pharmacokinetic properties. *Journal of Medicinal Chemistry*, 50(21): 5217-5226.
International Search Report and Written Opinion for PCT/US2013/023008, dated Apr. 2, 2013.

* cited by examiner

*Primary Examiner* — Janet L Andres
*Assistant Examiner* — Timothy R Rozof
(74) *Attorney, Agent, or Firm* — Baker Botts, LLP

(57) ABSTRACT

The present invention relates to compounds that exhibit vasodilatory and anti-inflammatory effects by inhibiting the activity of soluble epoxide hydrolase (sEH). The present invention is also directed to methods of identifying such compounds, and use of such compounds for the treatment of diseases related to dysfunction of vasodilation, inflammation, and/or endothelial cells. In particular non-limiting embodiments, components of the invention may be used to treat hypertension.

14 Claims, 9 Drawing Sheets

Table 3. The biological results for the tail modification.

| Comp | R² | Inhibition (%) at 200nm | IC50 (nm)[a] | Comp | R² | Inhibition (%) at 200nm | IC50 (nm) |
|---|---|---|---|---|---|---|---|
| 1 | mesityl-SO2 | 97 | 20.0[b] | 6-18 | 4-CF3-2-NO2-C6H3-SO2 | 37 | ND |
| 6-1 | 4-Me-C6H4-SO2 | 15 | ND[c] | 6-19 | 4-Br-C6H4-SO2 | 32 | ND |
| 6-2 | 2-NO2-C6H4-SO2 | 47 | ND | 6-20 | 4-Me-2-NO2-C6H3-SO2 | 28 | ND |
| 6-3 | 3-NO2-C6H4-SO2 (with SO2) | 45 | ND | 6-21 | 4-tBu-C6H4-SO2 | 85 | 164.0 |
| 6-4 | 3-Me-C6H4-SO2 | 21 | ND | 6-22 | 4-Cl-2,5-diMe-C6H2-SO2 | 97 | 52.1 |
| 6-5 | quinoline-8-SO2 | 34 | ND | 6-23 | 4-OCH3-2,3,5-triMe-C6H-SO2 | 98 | 23.9 |
| 6-6 | 3-Br-thiophene-2-SO2 | 43 | ND | 6-24 | 2,4-diMe-C6H3-SO2 | 97 | 46.9 |
| 6-6 | 2-Br-C6H4-SO2 | 63 | 91.1 | 6-25 | 3,5-di-tBu-C6H3-SO2 | 88 | 44.5 |

FIG. 4

| ID | Structure | Val1 | Val2 | ID | Structure | Val1 | Val2 |
|---|---|---|---|---|---|---|---|
| 6-7 | ClCH2CH2-SO2- | 31 | ND | 6-26 | mesityl ketone / NO2-phenyl | 34 | ND |
| 6-8 | 4-F-2-NO2-phenyl-SO2- | 63 | 150.0 | 6-27 | NO2-phenyl ketone | 18 | ND |
| 6-9 | 3-Br-quinoline-8-SO2- | 37 | ND | 6-28 | 3-SO2-phenyl ketone | 45 | ND |
| 6-10 | 2-F-phenyl-SO2- | 66 | 87.6 | 6-29 | 4-Br-phenyl ketone | 0 | ND |
| 6-11 | phenyl-SO2- | 45 | ND | 6-30 | mesityl-SO2-piperidine carbonyl | 33 | ND |
| 6-12 | 2-Cl-thiophene-SO2- | 52 | 200.0 | 6-31 | 4,5-(OCH3)2-2-NO2-phenyl ester | 71 | 75.3 |
| 6-13 | cyclohexyl-SO2- | 27 | ND | 6-32 | 4-NO2-phenyl ester | 41 | ND |
| 6-14 | isopropyl-SO2- | 13 | ND | 6-33 | thiophene-2-carbonyl | 16 | ND |
| 6-15 | 2-CF3-phenyl-SO2- | 39 | ND | 6-34 | 3-carbonyl-phenyl ketone | 55 | 200.0 |
| 6-16 | 2-Cl-quinoline-8-SO2- | 30 | ND | 6-35 | 2-NO2-phenyl ester | 44 | ND |
| 6-17 | 4-NHAc-phenyl-SO2- | 53 | ND | 6-36 | PPh2- | 3 | ND |

FIG.4-1

Table 2. The biological results for the head modification.

| Comp | R' | Inhibition(%) at 200nm | IC$_{50}$(nm) | Comp | R' | Inhibition(%) at 200nm | IC$_{50}$(nm)$^a$ |
|---|---|---|---|---|---|---|---|
| 8-1 | | 87 | 25.1 | 8-26 | | 44 | ND |
| 8-2 | | 55 | 39.4 | 8-27 | | 62 | 49.1 |
| 8-3 | | 78 | 35 | 8-28 | | 90 | 27.4 |
| 8-4 | | -4 | ND$^c$ | 8-29 | | 65 | 64.0 |
| 8-5 | | -1 | ND | 8-30 | | 98 | 59.1 |
| 8-6 | | -16 | ND | 8-31 | | 97 | 32.2 |
| 8-7 | | 3 | ND | 8-32 | | 96 | 173.0 |

| | | | | | | |
|---|---|---|---|---|---|---|
| 8-8 | [benzyl] | 48 | ND | 8-33 | [F3C, Cl-benzyl] | 94 | 28.7 |
| 8-9 | [benzyl] | 65 | 42.0 | 8-34 | [Cl, Cl-benzyl] | 94 | 29.1 |
| 8-10 | [naphthyl] | 50 | 200.0 | 8-35 | [Ph, Cl-benzyl] | 7 | ND |
| 8-11 | [Cl-naphthyl] | 44 | ND | 8-36 | [Cl-benzyl] | 98 | 54.1 |
| 8-12 | [t-Bu] | −7 | ND | 8-37 | [Cl, F-benzyl] | 97 | 12.7[b] |
| 8-13 | [morpholine] | −29 | ND | 8-38 | [Cl, F-benzyl] | 95 | 128.0 |
| 8-14 | [cyclohexylmethyl] | 87 | 16.4 | 8-39 | [Cl, Cl-benzyl] | 97 | 50.0 |
| 8-15 | [benzothiazole] | −17 | ND | 8-40 | [Me-benzyl] | 97 | 32.0 |
| 8-16 | [OMe-benzothiazole] | −18 | ND | 8-41 | [Cl, Cl-benzyl] | 77 | 37.2[b] |
| 8-17 | [F-benzothiazole] | −6 | ND | 8-42 | [cyclohexyl] | 90 | 7.9[b] |
| 8-18 | [pyridyl] | 23 | ND | 8-43 | [cycloheptyl] | 55 | 200.0 |
| 8-19 | [pyridyl] | 49 | ND | 8-44 | [Boc-piperidinyl] | 88 | 11.0[b] |

FIG.5-1

| | | | | |
|---|---|---|---|---|
| 8-20 | 62 | 33.6 | 8-45 | 79 | 20.1 |
| 8-21 | 67 | 43.3 | 8-46 | 86 | 39.6[b] |
| 8-22 | 16 | ND | 8-47 | 92 | 12.6[b] |
| 8-23 | −25 | ND | 8-48 | 75 | 37.3[b] |
| 8-24 | 9 | ND | 8-49 | 14 | ND |
| 8-25 | −6 | ND | 8-50 | 15 | ND |

FIG. 5-2

POTENT NON-UREA INHIBITORS OF SOLUBLE EPOXIDE HYDROLASE

CROSS-REFERENCE TO RELATED APPLICATION

The present application is a Continuation of PCT/US2009/057553, filed Sep. 18, 2009, which claims the benefit of U.S. Provisional Application No. 61/143,397, filed Jan. 8, 2009, both of which are hereby incorporated by reference in their entireties.

GRANT INFORMATION

The subject matter of the invention was developed, at least in part, under National Institutes of Health Grant No. MLSCN. The United States Government has certain rights herein.

1. INTRODUCTION

The present invention relates to compounds that exhibit vasodilatory and anti-inflammatory effects by inhibiting the activity of the enzyme soluble epoxide hydrolase (sEH). The present invention is also directed to the use of such compounds for the treatment of diseases related to dysfunction of vasodilation, inflammation, and/or endothelial cell function. In particular non-limiting embodiments, components of the invention may be used to treat hypertension.

2. BACKGROUND OF THE INVENTION

Epoxide hydrolases are a group of enzymes that are ubiquitous in nature, detected in species ranging from plants to mammals. These enzymes are functionally related in that they catalyze the addition of water to an epoxide, resulting in a diol. One subtype of epoxide hydrolase is the soluble epoxide hydrolase (sEH). sEH plays an important role in the metabolism of lipid epoxides. Endogenous substrates of sEH include epoxyeicosatrienoic acids (EETs), which are effective regulators of blood pressure and inflammation.

The metabolism of arachidonic acid by cytochrome P450 monoxygenase leads to the formation of various biologically active eicosanoids, and is the primary route of EET synthesis. Three types of oxidative reactions are known to occur to the precursor eicosanoids, and one of these, olefin epoxidation (catalyzed by epoxygenases), produces EETs. Four important EET regioisomers are [5,6]-EET, [8,9]-EET, [11.12]-EET, and [14,15]-EET. These arachidonic acid derivatives function as lipid mediators in certain tissues, potentially through receptor-ligand interactions, and further, can be incorporated into tissue phospholipids (Bernstrom et al. 1992, J. Biol. Chem. 267:3686-3690).

Hypertension has been shown to result from an impairment of endothelium dependent vasodilation (Lind, et al., Blood Pressure, 9: 4-15 (2000)). In healthy individuals, endothelium derived hyperpolarizing factor, EDHF, hyperpolarizes vascular smooth muscle tissue resulting in endothelium-dependent relaxation. EETs are known to provoke signaling pathways which lead to cell membrane hyperpolarization, and therefore have been considered as a candidate EDHF. In vascular tissue, hyperpolarization by EETs results in increased coronary blood flow and improved recovery of myocardium from ischemia-reperfusion injury. (Wu et al., 272 J. Biol. Chem. 12551 (1997); Oltman et al., 83 Circ. Res. 932 (1998)). Accordingly, EETs are predicted to be useful in the treatment of hypertension as well as ischemia-related damage and disease.

In addition to promoting vasodilation, EETs have also been shown to exhibit anti-inflammatory properties. For example, 11,12-EET can reduce inflammation by decreasing the expression of cytokine induced endothelial cell adhesion molecules (such as VCAM-1) (Node, et al., Science, 285: 1276-1279 (1999); Campbell, TIPS, 21: 125-127 (2000); Zeldin and Liao, TIPS, 21: 127-128 (2000)). Other studies have demonstrated that EETs can inhibit vascular inflammation by inhibiting NF-κB and IκB, which prevents leukocyte adhesion to vascular cell walls. As such, EETs are also predicted to be useful in reducing inflammation and alleviating endothelial cell dysfunction (Kessler, et al., Circulation, 99: 1878-1884 (1999)).

Hydrolysis of EETs by sEH converts the EETs to corresponding diols. Such diols have been shown to exhibit diminished vasodilatory and anti-inflammatory effects (Smith et al., 2005, Proc. Natl. Acad. Sci. USA. 102:2186-91; and Schmelzer et al., 2005, Proc. Natl. Acad. Sci. USA. 102: 9772-7). As inhibition of sEH leads to accumulation of active EETs, such inhibition provides a novel approach to the treatment of hypertension and vascular inflammation (Chiamvimonvat et al., 2007, J. Cardiovasc. Pharmacol. 50:225-37). To date, the most successful sEH inhibitors reported are 1,3-disubstituted ureas. These urea-based inhibitors have been shown to treat hypertension and inflammatory diseases through inhibition of EET hydrolysis in several animal models. However, these inhibitors often suffer from poor solubility and bioavailability, which makes them less therapeutically efficient (Wolf et al., 2006, J. Med. Chem. 335:71-80). Therefore there remains a need for identifying new sEH inhibitors for therapeutic application.

3. SUMMARY OF THE INVENTION

The present invention relates to compounds of Formula I:

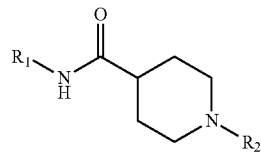

wherein $R^1$ and $R^2$ are described herein below. The present invention also provides salts, esters and prodrugs of the compounds of Formula I.

Additionally, the present invention describes methods of synthesizing compounds of Formula I.

The present invention further provides a method of inhibiting the activity of soluble epoxide hydrolase (sEH), by contacting the sEH with a compound of Formula I in an amount effective to inhibit the activity of sEH.

In one embodiment, the sEH is expressed by a cell, for example, a mammalian cell, and the cell is contacted with the compound of Formula I.

In another embodiment, the sEH is contacted with the compound of Formula I in vitro.

The present invention also provides a method of decreasing the metabolism of an epoxyeicosatrienoic acid (EET), and thus increasing the level of an EET, by contacting an sEH with a compound of Formula I in an amount effective to increase the level of an EET.

The present invention also provides compositions comprising a compound of Formula I and a pharmaceutically acceptable carrier.

Also provided is a method for treating, preventing, or controlling diseases related to dysfunction of vasodilation, inflammation, and/or endothelial cells by administering to an individual in need of such treatment a pharmaceutical composition comprising a compound of Formula I in an amount effective to inhibit sEH activity or increase the level of EETs in the individual.

Also provided is a method for treating, preventing, or controlling metabolic syndrome by administering to an individual in need of such treatment a pharmaceutical composition comprising a compound of Formula I in an amount effective to inhibit sEH activity or increase the level of EETs in the individual.

4. BRIEF DESCRIPTION OF THE DRAWINGS

FIG. 4 Shows compounds and their biological results for the tail (i.e. $R^2$) modifications of compound 1.

Figure 6:
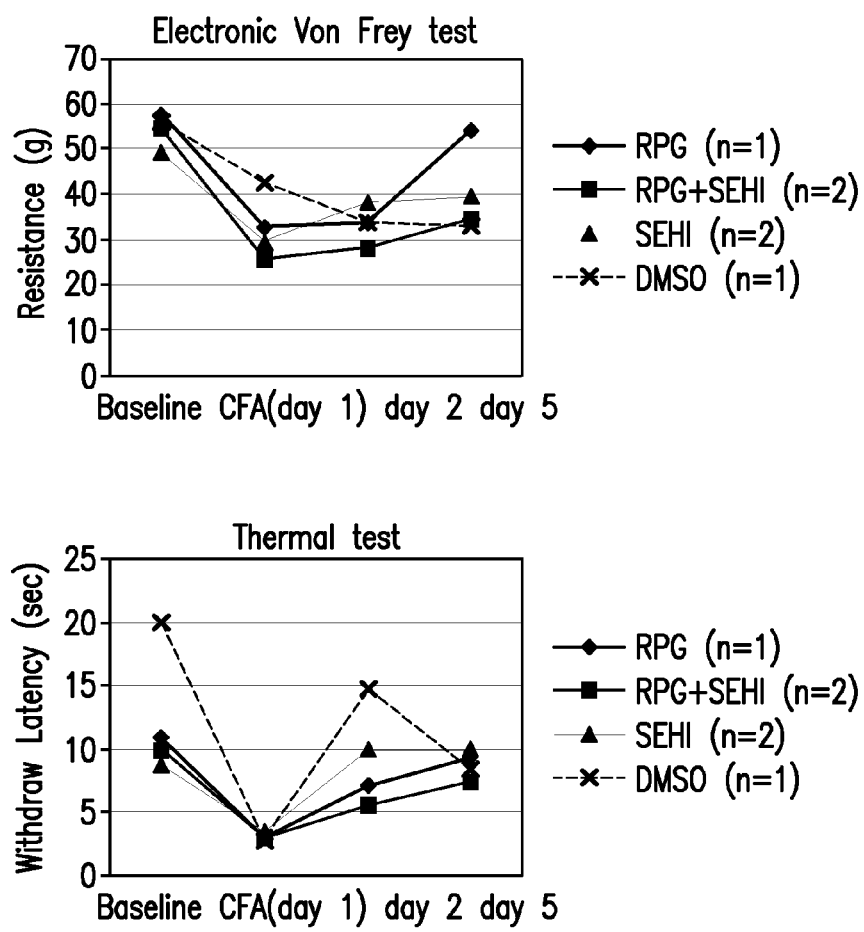

FIG. 6 Shows the in vivo effect of compound 8-42 on inflammation to induced by Complete Freund's Adjuvant (CFA). Inflammation was assayed by determining pain threshold using electronic Von Frey and thermal testing. A baseline pain threshold was determined before CFA administration. CFA was administered at day 1, and 8-42 or control agents were administered 24 hours later. Pain threshold was measured on days 1, 2 and 5.

5. DETAILED DESCRIPTION

The present invention is based on the discovery of compounds that inhibit sEH enzymatic activity and increase the level of EETs in a cell. In light of the role EETs play in connection with vasodilation, inflammation, and endothelial cell function, the compounds of the instant invention can be used to increase EET levels and thereby ameliorate pathologies associated with diseases relating to vasodilation dysregulation, inflammation, and/or endothelial cell dysfunction.

For clarity and not by way of limitation, this detailed description is divided into the following sub-portions:

(i) definitions;
(ii) sEH inhibitors;
(iii) methods of treatment; and
(iv) pharmaceutical compositions.

5.1 Definitions

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

The terms "soluble epoxide hydrolase" and "sEH" refer to a polypeptide which catalyzes the addition of water to an epoxide substrate, resulting in a diol. In one non-limiting embodiment the epoxide substrate is a lipid epoxide. In another non-limiting embodiment, the substrate is an epoxyeicosatrienoic acid (EET).

In one non-limiting embodiment, a soluble epoxide hydrolase which may be inhibited according to the invention is a human soluble epoxide hydrolase. Such soluble epoxide hydrolase may, for example, be encoded by the human epoxide hydrolase 2, cytoplasmic gene (EPHX2) (GenBank accession number NM_001979), a nucleic acid which encodes the human soluble epoxide hydrolase polypeptide. Alternatively, soluble epoxide hydrolase can be encoded by any nucleic acid molecule exhibiting at least 50%, at least 60%, at least 70%, at least 80%, at least 90% or up to 100% homology to the EPHX2 gene (as determined by standard software, e.g. BLAST or FASTA), and any sequences which hybridize under standard conditions to these sequences.

In other non-limiting embodiments, a soluble epoxide hydrolase which may be inhibited according to the invention may be characterized as having an amino acid sequence described by GenBank accession numbers: AAG14968, AAG14967, AAG14966 and NP_001970, or any other amino acid sequence at least 90% homologous thereto.

The soluble epoxide hydrolase may be a recombinant sEH polypeptide encoded by a recombinant nucleic acid, for example, a recombinant DNA molecule, or may be of natural origin.

The terms "epoxyeicosatrienoic acid" and "EET" refer to a substrate of the soluble epoxide hydrolase enzyme. For example, an epoxyeicosatrienoic acid may have the following generic Formula II:

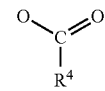

wherein $R_4$ is $C_{19}H_{31}$, and wherein an epoxide is bound to any two consecutive carbons of Formula II, and further, wherein any two consecutive carbons may be covalently bonded to each other by a double bond.

Substrate EETs, the cleavage of which are inhibited according to the invention, include effective regulators of blood pressure and cardiovascular function and/or inflammation.

In one such non-limiting embodiment, EET is an eicosanoid produced by the metabolic activity of a Cytochrome P450 epoxygenase on a fatty acid, such as arachidonic acid.

In another such non-limiting embodiment, the EET is a [5,6]-EET, as depicted in Formula III:

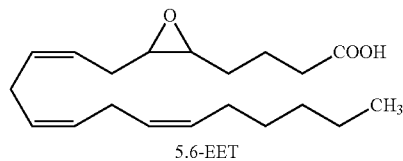 [SMILES: CCCCC/C=C\C/C=C\C/C=C\CC1OC1CCCC(=O)O]

5,6-EET

In another such non-limiting embodiment, the EET is a [8,9]-EET, as depicted in Formula IV:

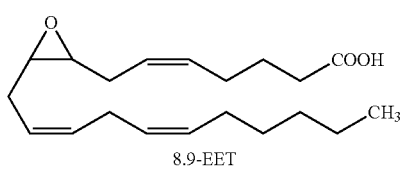 [SMILES: CCCCC/C=C\C/C=C\CC1OC1C/C=C\CCCC(=O)O]

8,9-EET

In another such non-limiting embodiment, the EET is a [11,12]-EET, as depicted in Formula V:

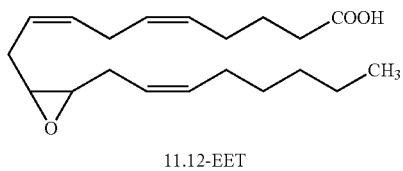 [SMILES: CCCCC/C=C\CC1OC1C/C=C\C/C=C\CCCC(=O)O]

11,12-EET

In yet another such non-limiting embodiment, the EET is a [14,15]-EET, as depicted in Formula VI:

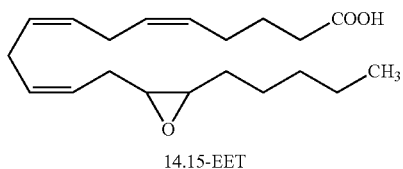 [SMILES: CCCCCC1OC1C/C=C\C/C=C\C/C=C\CCCC(=O)O]

14,15-EET

In yet another non-limiting embodiment, the EET can function as a lipid mediator and can be incorporated into tissue phospholipids (Bernstrom et al. 1992, J. Biol. Chem. 267:3686-3690).

The term "dysfunction of vasodilation" refers to the reduced capability of a blood vessel, for example, an artery or arteriole, to dilate normally in response to an appropriate stimulus, for example, an endothelium derived hyperpolarizing factor, EDHF, and may be manifested by an inappropriate blood pressure, e.g. hypertension.

The term "endothelial cell dysfunction" refers to a physiological dysfunction of normal biochemical processes carried out by endothelial cells, the cells that line the inner surface of all blood vessels including arteries and veins. For example, endothelial cell dysfunction may result in an inability of blood vessels, such as arteries and arterioles, to dilate normally in response to an appropriate stimulus.

The term "inflammation" encompasses both acute responses (i.e., responses in which the inflammatory processes are active) as well as chronic responses (i.e., responses marked by slow progression and formation of new connective tissue).

In certain non-limiting embodiments, a disease associated with a dysfunction of vasodilation, inflammation, and/or endothelial cells that is to be treated by a compound of the instant invention is, by way of example, but not by way of limitation, heart disease, hypertension, such as primary or secondary hypertension, an ischemic condition such as angina, myocardial infarction, transient ischemic neurologic attack, cerebral ischemia, ischemic cerebral infarction, bowel infarction or other ischemic damage to tissue associated with poor perfusion.

In other non-limiting embodiments, a disease associated with inflammation that may be treated by a compound of the instant invention is, by way of example, but not by way of limitation, type I hypersensitivity, atopy, anaphylaxis, asthma, osteoarthritis, rheumatoid arthritis, septic arthritis, gout, juvenile idiopathic arthritis, still's disease, ankylosing spondylitis, inflammatory bowel disease, Crohn's disease or inflammation associated with vertebral disc herniation.

The term "metabolic syndrome" refers to risk factors that indicate an increased risk of developing coronary heart disease, type 2 diabetes and other diseases related to plaque buildups in artery walls, such as, for example, atherosclerosis, stroke and peripheral vascular disease. Metabolic syndrome risk factors include, for example, abdominal obesity (i.e. excessive fat tissue in and around the abdomen), atherogenic dyslipidemia (i.e. blood fat disorders such as for example, high triglycerides, low HDL cholesterol and high LDL cholesterol, that foster plaque buildups in artery walls), elevated blood pressure, insulin resistance or glucose intolerance, prothrombotic state (e.g., high fibrinogen or plasminogen activator inhibitor-1 in the blood) and/or a proinflammatory state (e.g., elevated C-reactive protein in the blood).

The term 'alkyl' refers to a straight or branched $C_1$-$C_{20}$ (preferably $C_1$-$C_6$) hydrocarbon group consisting solely of carbon and hydrogen atoms, containing no unsaturation, and which is attached to the rest of the molecule by a single bond, e.g., methyl, ethyl, n-propyl, 1-methylethyl (isopropyl), n-butyl, n-pentyl, 1,1-dimethylethyl (t-butyl).

The term "alkenyl" refers to a $C_2$-$C_{20}$ (preferably $C_1$-$C_4$) aliphatic hydrocarbon group containing at least one carbon-carbon double bond and which may be a straight or branched chain, e.g., ethenyl, 1-propenyl, 2-propenyl (allyl), iso-propenyl, 2-methyl-1-propenyl, 1-butenyl, 2-butenyl.

The term "cycloalkyl" denotes an unsaturated, non-aromatic mono- or multicyclic hydrocarbon ring system (containing, for example, $C_3$-$C_6$) such as cyclopropyl, cyclobutyl, cyclopentyl, cyclohexyl. Examples of multicyclic cycloalkyl groups (containing, for example, $C_6$-$C_{15}$) include perhydronapththyl, adamantyl and norbornyl groups bridged cyclic group or sprirobicyclic groups, e.g., spiro (4,4) non-2-yl.

The term "cycloalkalkyl" refers to a cycloalkyl as defined above directly attached to an alkyl group as defined above, that results in the creation of a stable structure such as cyclopropylmethyl, cyclobutylethyl, cyclopentylethyl.

The term "alkyl ether" refers to an alkyl group or cycloalkyl group as defined above having at least one oxygen incorporated into the alkyl chain, e.g., methyl ethyl ether, diethyl ether, tetrahydrofuran.

The term "alkyl amine" refers to an alkyl group or a cycloalkyl group as defined above having at least one nitrogen atom, e.g., n-butyl amine and tetrahydrooxazine.

The term "aryl" refers to aromatic radicals having in the range of about 6 to about 14 carbon atoms such as phenyl, naphthyl, tetrahydronapthyl, indanyl, biphenyl.

The term "arylalkyl" refers to an aryl group as defined above directly bonded to an alkyl group as defined above, e.g., —$CH_2C_6H_5$, and —$C_2H_4C_6H_5$.

The term "heterocyclic" refers to a stable 3- to 15-membered ring radical which consists of carbon atoms and one or more, for example, from one to five, heteroatoms selected from the group consisting of nitrogen, oxygen and sulfur. For purposes of this invention, the heterocyclic ring radical may be a monocyclic or bicyclic ring system, which may include fused or bridged ring systems, and the nitrogen, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heteroaromatic or heteroaryl aromatic).

The heterocyclic ring radical may be attached to the main structure at any heteroatom or carbon atom that results in the creation of a stable structure.

The term "heteroaryl" refers to a heterocyclic ring wherein the ring is aromatic.

The term "heteroarylalkyl" refers to heteroaryl ring radical as defined above directly bonded to alkyl group. The heteroarylalkyl radical may be attached to the main structure at any carbon atom from alkyl group that results in the creation of a stable structure.

The term "heterocyclyl" refers to a heterocyclic ring radical as defined above. The heterocyclyl ring radical may be attached to the main structure at any heteroatom or carbon atom that results in the creation of a stable structure.

The term "halogen" refers to radicals of fluorine, chlorine, bromine and iodine.

5.2 sEH Inhibitors

The present invention provides compounds of the following Formula I:

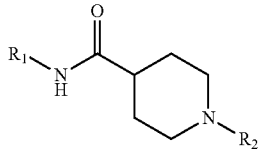

wherein $R^1$ and $R^2$ are independently selected for each occurrence from the group consisting of phosphorous (e.g., substituted phosphorous such as diphenylphosphine), substituted or unsubstituted benzothiazol, substituted or unsubstituted pyridyl, substituted or unsubstituted naphthyl, substituted or unsubstituted phenyl, substituted or unsubstituted alkyl, substituted or unsubstituted cycloalkyl, substituted or unsubstituted aryl, substituted or unsubstituted cycloalkalkyl, substituted or unsubstituted arylalkyl, substituted or unsubstituted heteroarylalkyl, substituted or unsubstituted heteroaryl, substituted or unsubstituted heterocyclic, —C(O)$R^3$ and —S(O)$_2R^3$, wherein $R^3$ is independently selected for each occurrence from the groups consisting of substituted or unsubstituted alkyl, substituted or unsubstituted cycloalkyl; substituted or unsubstituted aryl; substituted or unsubstituted arylalkyl; substituted or unsubstituted heteroaryl; substituted or unsubstituted heterocyclic, substituted or unsubstituted naphthyl, substituted or unsubstituted phenyl, substituted or unsubstituted thienyl, substituted or unsubstituted benzothienyl, substituted or unsubstituted pyridyl, substituted or unsubstituted indol, substituted or unsubstituted isoquinolyl, substituted or unsubstituted quinolyl, and substituted or unsubstituted benzothiazol.

The substituents in the 'substituted alkyl', 'substituted cycloalkyl', 'substituted cycloalkalkyl', 'substituted arylalkyl', 'substituted aryl', 'substituted heterocyclic', 'substituted heteroarylalkyl,' 'substituted heteroaryl', 'substituted naphthyl', 'substituted phenyl', 'substituted thienyl', 'substituted benzothienyl', 'substituted pyridyl', 'substituted indol', 'substituted isoquinolyl', 'substituted quinolyl', or 'substituted benzothiazol' may be the same or different with one or more selected from the groups hydrogen, halogen, acetyl, nitro, oxo (═O), thio (═S), —NO$_2$, —CF$_3$, —OCH$_3$, —Boc or optionally substituted groups selected from alkyl, alkoxy, aryl, arylalkyl, heteroaryl, and heterocyclic ring. A "substituted" functionality may have one or more than one substituent.

In one preferred non-limiting embodiment, $R^1$ is an unsubstituted cycloalkyl.

In other preferred non-limiting embodiments, $R^1$ is an unsubstituted or substituted aryl having one or more substituent which is a halogen, more preferably fluorine or chlorine (where multiple substituents are present they may be the same or different).

In preferred non-limiting embodiments, $R^2$ is —S(O)$_2R^3$. In specific preferred non-limiting embodiments $R^3$ is a substituted or unsubstituted aryl. In further specific preferred non-limiting embodiments, $R^2$ is —S(O)$_2R^3$, where $R^3$ is a substituted aryl and the one or more substituent is selected from the group consisting of a hydrophobic alkyl group(s), such as the methyl group(s) present on toluene, xylene, and mesitylene, and a halide. In preferred non-limiting embodiments, at least one of said substituent of —S(O)$_2R^3$, where $R^3$ is a substituted aryl, is in the ortho position. In preferred non-limiting embodiments, the substituent of —S(O)$_2R^3$, where $R^3$ is a substituted aryl, is a bromide or fluoride or methyl at the ortho position.

In non-limiting embodiments within the scope of Formula I, the present invention provides compounds of the following Formula VII:

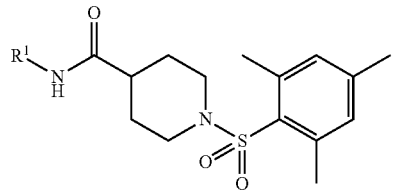

wherein $R^1$ is selected from the group consisting of phosphorous (e.g., substituted phosphorous such as diphenylphosphine), substituted or unsubstituted benzothiazol, substituted or unsubstituted pyridyl, substituted or unsubstituted naphthyl, substituted or unsubstituted phenyl, substituted or unsubstituted alkyl, substituted or unsubstituted cycloalkyl, substituted or unsubstituted aryl, substituted or unsubstituted cycloalkalkyl, substituted or unsubstituted arylalkyl, substituted or unsubstituted heteroarylalkyl, substituted or unsubstituted heteroaryl, substituted or unsubstituted heterocyclic, —C(O)$R^3$ and —S(O)$_2R^3$, wherein $R^3$ is independently selected for each occurrence from the groups consisting of substituted or unsubstituted alkyl, substituted or unsubstituted cycloalkyl: substituted or unsubstituted aryl; substituted or unsubstituted arylalkyl; substituted or unsubstituted heteroaryl; substituted or unsubstituted heterocyclic, substituted or unsubstituted naphthyl, substituted or unsubstituted phenyl, substituted or unsubstituted thienyl, substituted or unsubstituted benzothienyl, substituted or unsubstituted pyridyl, substituted or unsubstituted indol, substituted or unsubstituted isoquinolyl, substituted or unsubstituted quinolyl, and substituted or unsubstituted benzothiazol.

The substituents in the 'substituted alkyl', 'substituted cycloalkyl', 'substituted cycloalkalkyl', 'substituted arylalkyl', 'substituted aryl', 'substituted heterocyclic', 'substituted heteroarylalkyl,' 'substituted heteroaryl', 'substituted naphthyl', 'substituted phenyl', 'substituted thienyl', 'substituted benzothienyl', 'substituted pyridyl', 'substituted indol', 'substituted isoquinolyl', 'substituted quinolyl', or 'substituted benzothiazol' may be the same or different with one or more selected from the groups hydrogen, halogen, acetyl, nitro, oxo (═O), thio (═S), —NO$_2$, —CF$_3$, —OCH$_3$, —Boc or optionally substituted groups selected from alkyl, alkoxy, aryl, arylalkyl, heteroaryl, and heterocyclic ring. A "substituted" functionality may have one or more than one substituent.

In one non-limiting embodiment, when $R^1$ is a substituted phenyl, and the substituent is an unsubstituted alkyl, the alkyl is at least a $C_3$ alkyl, for example, a propyl or butyl.

In further non-limiting embodiments of the invention, $R^1$ in Formula I or Formula VII is selected from the compounds listed in Table 1:

TABLE 1

| Compound | $R^1$ |
|---|---|
| 8-1 | 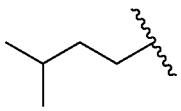 [SMILES: *CCC(C)C] |
| 8-2 | 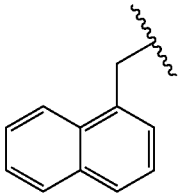 [SMILES: *Cc1cccc2ccccc12] |
| 8-3 | 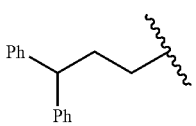 [SMILES: *CCC(c1ccccc1)c1ccccc1] |
| 8-4 | 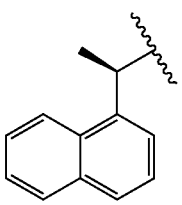 [SMILES: *[C@H](C)c1cccc2ccccc12] |
| 8-5 | 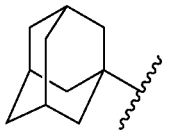 [SMILES: *C12CC3CC(CC(C3)C1)C2] |
| 8-6 | 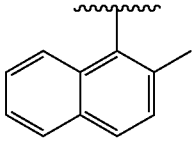 [SMILES: *c1c(C)ccc2ccccc12] |
| 8-7 | 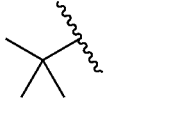 |
| 8-8 | 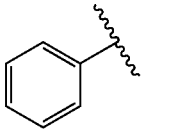 [SMILES: *c1ccccc1] |

TABLE 1-continued

| Compound | $R^1$ |
|---|---|
| 8-9 | 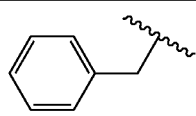 |
| 8-10 | 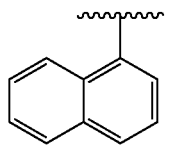 [SMILES: *c1cccc2ccccc12] |
| 8-11 | 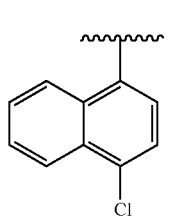 [SMILES: *c1ccc(Cl)c2ccccc12] |
| 8-12 | 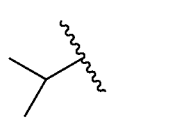 [SMILES: *C(C)C] |
| 8-13 | 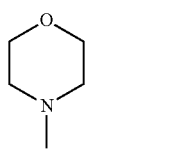 |
| 8-14 | 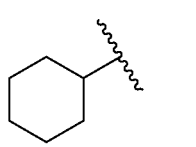 [SMILES: *C1CCCCC1] |
| 8-15 | 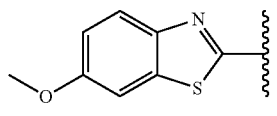 [SMILES: *c1nc2ccc(OC)cc2s1] |
| 8-16 | 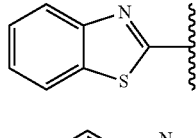 |
| 8-17 | 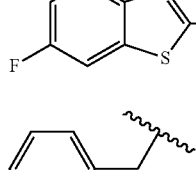 |
| 8-18 | 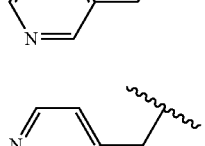 |
| 8-19 | 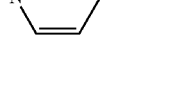 |

TABLE 1-continued
| Compound | R¹ |
|---|---|
| 8-20 | 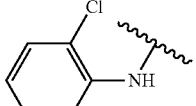 |
| 8-21 | 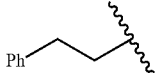 |
| 8-22 | 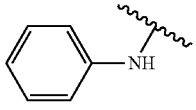 [SMILES: *Nc1ccccc1] |
| 8-23 | 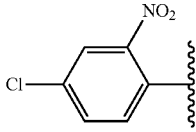 [SMILES: *c1ccc(Cl)cc1[N+](=O)[O-]] |
| 8-24 | 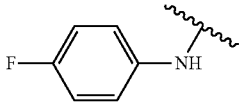 [SMILES: *Nc1ccc(F)cc1] |
| 8-25 | 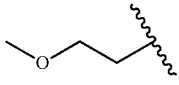 [SMILES: *CCOC] |
| 8-26 | 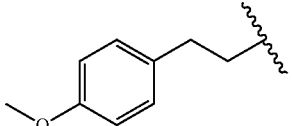 |
| 8-27 | 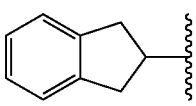 [SMILES: *C1Cc2ccccc2C1] |
| 8-28 | 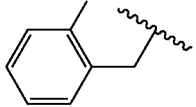 |
| 8-29 | 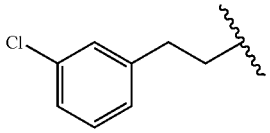 [SMILES: *CCc1cccc(Cl)c1] |
| 8-30 | 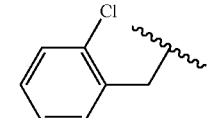 |
| 8-31 | 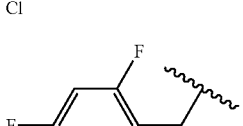 |
| 8-32 | 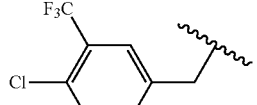 |
| 8-33 | 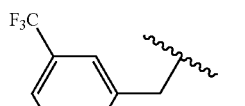 |
| 8-34 | 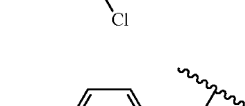 |
| 8-35 | 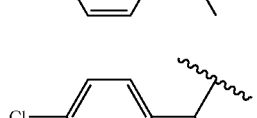 |
| 8-36 | 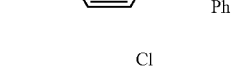 |
| 8-37 | 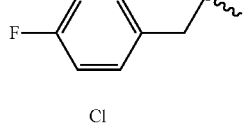 |
| 8-38 | 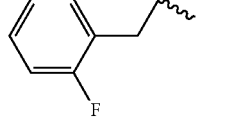 |
| 8-39 | 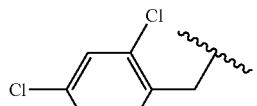 |
| 8-40 | 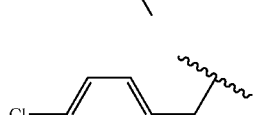 |
| 8-41 | 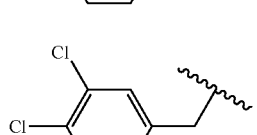 |

TABLE 1-continued

| Compound | R¹ |
|---|---|
| 8-42 | 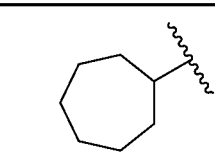 |
| 8-43 | |
| 8-44 | |
| 8-45 | |
| 8-46 | |
| 8-47 | |
| 8-48 | |
| 8-49 | |
| 8-50 | |

In preferred non-limiting embodiments, R¹ in Formula I or Formula VII is selected from the group consisting of the following compounds:

(8-9) 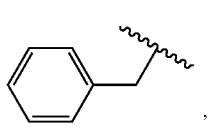

(8-14) 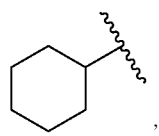

(8-37) 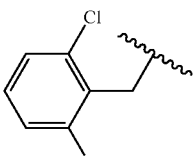

(8-42) 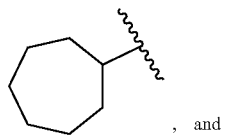

, and (8-47) 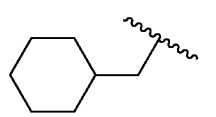

In other non-limiting embodiments within the scope of Formula I, the present invention provides compounds of the following Formula VIII:

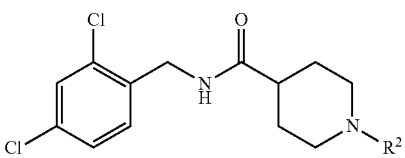

wherein R² is selected from the group consisting of phosphorous (e.g., substituted phosphorous such as diphenylphosphine), substituted or unsubstituted to benzothiazol, substituted or unsubstituted pyridyl, substituted or unsubstituted naphthyl, substituted or unsubstituted phenyl, substituted or unsubstituted alkyl, substituted or unsubstituted cycloalkyl, substituted or unsubstituted aryl, substituted or unsubstituted cycloalkalkyl, substituted or unsubstituted arylalkyl, substituted or unsubstituted heteroarylalkyl, substituted or unsubstituted heteroaryl, substituted or unsubstituted heterocyclic, —C(O)R³ and —S(O)₂R³, wherein R³ is independently selected for each occurrence from the groups consisting of substituted or unsubstituted alkyl, substituted or unsubstituted cycloalkyl; substituted or unsubstituted aryl; substituted or unsubstituted arylalkyl; substituted or unsubstituted heteroaryl; substituted or unsubstituted heterocyclic, substituted or unsubstituted naphthyl, substituted or unsubstituted phenyl, substituted or unsubstituted thienyl, substituted or unsubstituted benzothienyl, substituted or unsubstituted pyridyl, substituted or unsubstituted indol, substituted or unsubstituted isoquinolyl, substituted or unsubstituted quinolyl, and substituted or unsubstituted benzothiazol.

The substituents in the 'substituted alkyl', 'substituted cycloalkyl', 'substituted cycloalkalkyl', 'substituted arylalkyl', 'substituted aryl', 'substituted heterocyclic', 'substituted heteroarylalkyl,' 'substituted heteroaryl', 'substituted naphthyl', 'substituted phenyl', 'substituted thienyl', 'substituted benzothienyl', 'substituted pyridyl', 'substituted indol', 'substituted isoquinolyl', 'substituted quinolyl', or 'substituted benzothiazol' may be the same or different with one or more selected from the groups hydrogen, halogen, acetyl, nitro, oxo (=O), thio (=S), —NO₂, —CF₃, —OCH₃, —Boc or optionally substituted groups selected from alkyl, alkoxy, aryl, arylalkyl, heteroaryl, and heterocyclic ring. A "substituted" functionality may have one or more than one substituent.

In preferred non-limiting embodiments, $R^2$ is $—S(O)_2R^3$. In specific preferred non-limiting embodiments $R^3$ is a substituted or unsubstituted aryl. In further specific preferred non-limiting embodiments, $R^2$ is $—S(O)_2R^3$, where $R^3$ is a substituted aryl and the one or more substituent is selected from the group consisting of a hydrophobic alkyl group(s), such as the methyl group(s) present on toluene, xylene, and mesitylene, and a halide. In preferred non-limiting embodiments, at least one of said substituent of $—S(O)_2R^3$, where $R^3$ is a substituted aryl, is in the ortho position. In preferred non-limiting embodiments, the substituent of $—S(O)_2R^3$, where $R^3$ is a substituted aryl, is a bromide or fluoride or methyl at the ortho position.

In specific non-limiting embodiments of the invention, $R^2$ in Formula I or VIII is selected from the compounds listed in Table 2:

TABLE 2

| Compound | $R^2$ |
| --- | --- |
| 1 | (2,4,6-trimethylphenylsulfonyl) |
| 6-1 | (4-methylphenylsulfonyl) |
| 6-2 | (2-nitrophenylsulfonyl) |
| 6-3 | (1,3-phenylenedisulfonyl) |
| 6-4 | (3-nitrophenylsulfonyl) |
| 6-5 | (quinolin-5-ylsulfonyl) |
| 6-6(a) | (5-bromothiophen-2-ylsulfonyl) |
| 6-6(b) | (2-bromophenylsulfonyl) |
| 6-7 | (2-chloroethylsulfonyl) |
| 6-8 | (4-fluoro-2-nitrophenylsulfonyl) |
| 6-9 | (4-bromoisoquinolin-5-ylsulfonyl) |
| 6-10 | (2-fluorophenylsulfonyl) |
| 6-11 | (methylsulfonyl) |
| 6-12 | (5-chlorothiophen-2-ylsulfonyl) |
| 6-13 | (cyclohexylsulfonyl) |
| 6-14 | (isopropylsulfonyl) |
| 6-15 | (2-(trifluoromethyl)phenylsulfonyl) |

TABLE 2-continued

| Compound | R² |
|---|---|
| 6-16 | 5-sulfonyl-1-chloroisoquinoline |
| 6-17 | 4-NHAc-phenyl-SO₂ |
| 6-18 | 2-NO₂-4-CF₃-phenyl-SO₂ |
| 6-19 | 4-Br-phenyl-SO₂ |
| 6-20 | 4-methyl-2-NO₂-phenyl-SO₂ |
| 6-21 | 4-tBu-phenyl-SO₂ |
| 6-22 | 4-Cl-2,5-dimethyl-phenyl-SO₂ |
| 6-23 | 4-OCH₃-2,5-dimethyl-phenyl-SO₂ |
| 6-24 | 2,4-dimethyl-phenyl-SO₂ |
| 6-25 | 2,4,6-tri-tBu-phenyl-SO₂ |
| 6-26 | 2,4,6-trimethyl-benzoyl |
| 6-27 | 3-NO₂-benzoyl |
| 6-28 | 3-(SO₂)-benzoyl |
| 6-29 | 4-Br-benzoyl |
| 6-30 | 4-(mesityl-SO₂)-piperidinyl-carbonyl |
| 6-31 | 4,5-dimethoxy-2-NO₂-phenoxy-carbonyl |
| 6-32 | 4-NO₂-phenoxy-carbonyl |
| 6-33 | thiophene-2-carbonyl |
| 6-34 | 1,3-phenylene-dicarbonyl |
| 6-35 | 2-NO₂-benzoyl |

TABLE 2-continued

| Compound | R² |
|---|---|
| 6-36 | 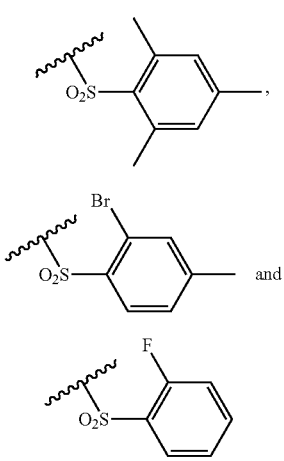 |

In other preferred non-limiting embodiments, R² in Formula I or Formula VIII is selected from the group consisting of the following compounds:

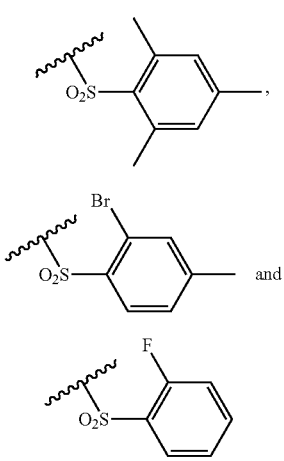

(1)

(6-6)

(6-10)

In another preferred embodiment, the compound defined by Formula I, Formula VII and/or Formula VIII is selected from the group consisting of the following compounds:

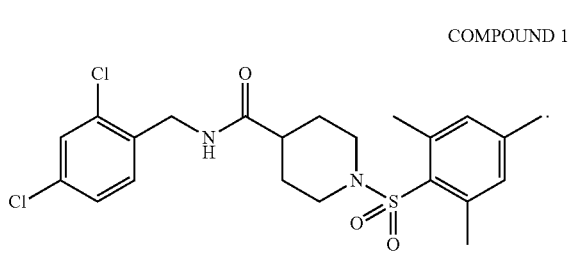

COMPOUND 1

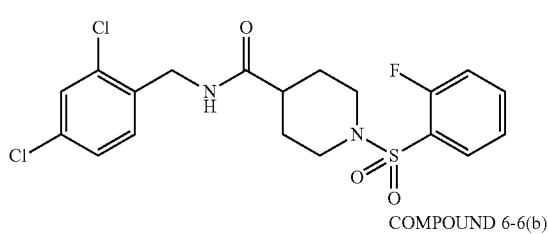

COMPOUND 6-10

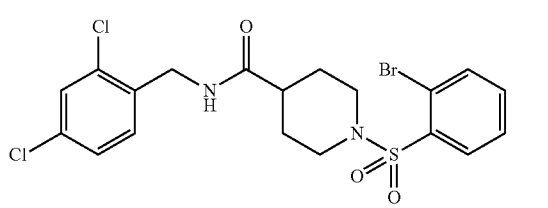

COMPOUND 6-6(b)

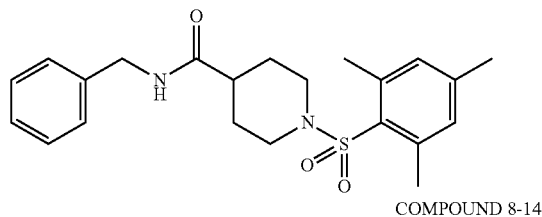

COMPOUND 8-9

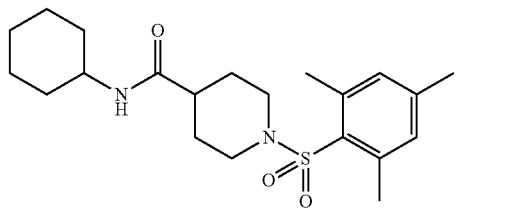

COMPOUND 8-14

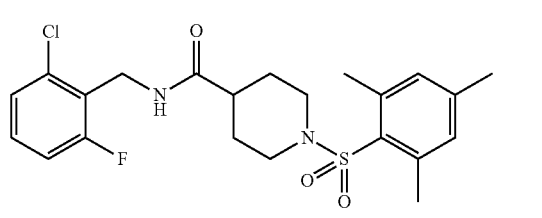

COMPOUND 8-37

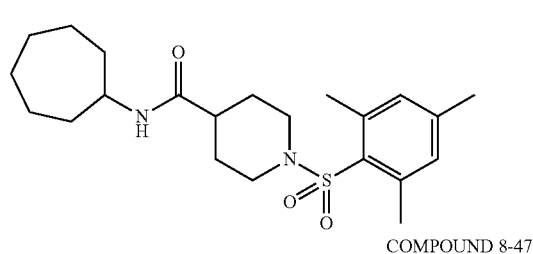

COMPOUND 8-42

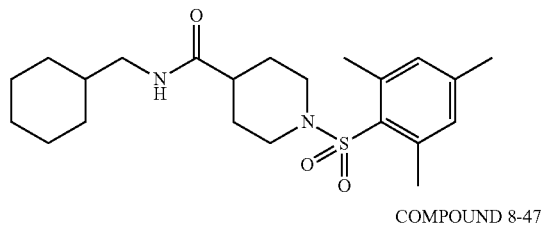

COMPOUND 8-47

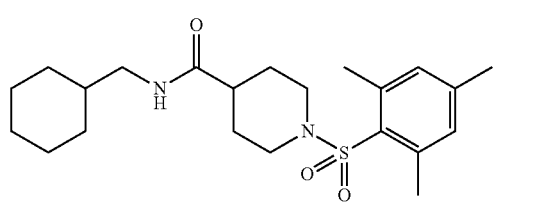

COMPOUND 8-47

Compounds of Formula I may, without limitation, be synthesized by any means known in the art. For example, methyl isonipecotate may be protected with benzyl chloroformate, and then converted into an acid chloride by removing the methyl ester followed by treatment with oxalyl chloride. Coupling of the acid chloride with 2,4-dichlorobenzylamine followed by Palladium catalyzed hydrogenation produces an amine, which may be reacted with a variety of sulfonyl chlorides, acid chlorides and chloroformates to produce compounds 6-6 and 6-10.

In other non-limiting embodiments, Methyl isonipecotate may be treated with mesitylenesulphonyl chloride followed by conversion into acid chloride by removing the methyl ester followed by treatment with oxalyl chloride. The acid chloride may then be reacted with various amines to produce compounds 8-9, 8-14, 8-37, 8-42, and 8-47

In other non-limiting embodiments, the compounds of Formula I, VII and VIII may be synthesized according to the following scheme:

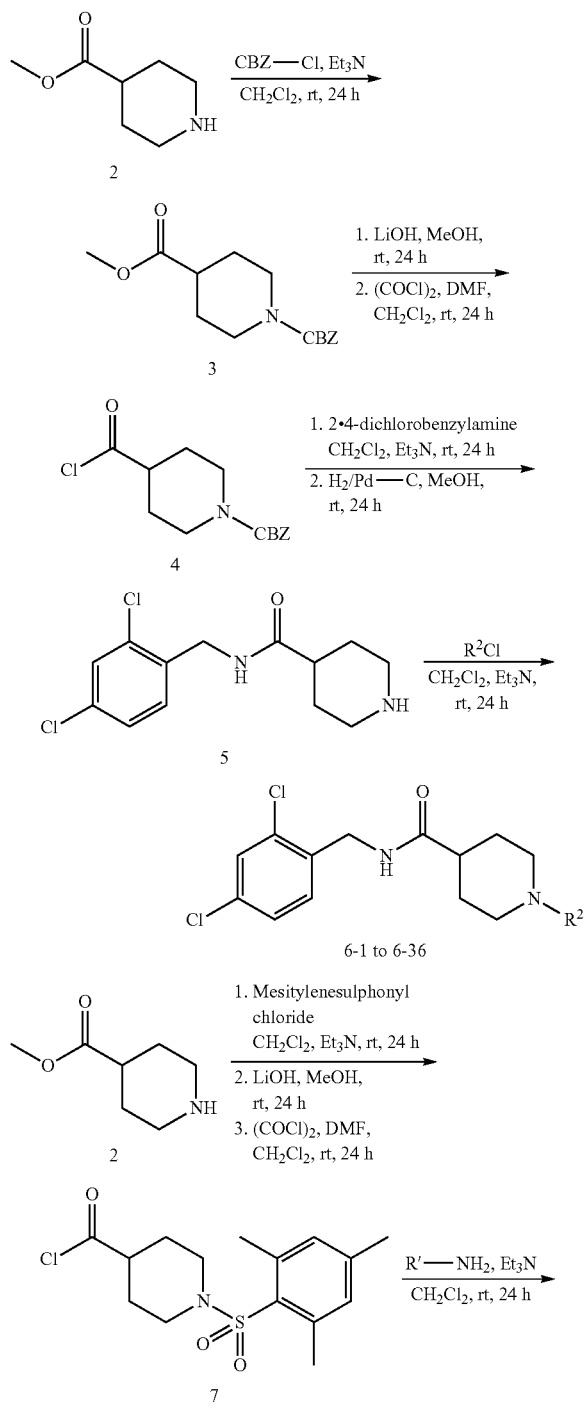

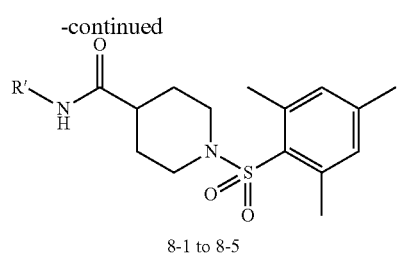

8-1 to 8-5 wherein $R^1$ and $R^2$ are selected from the compounds listed in Table 2 and Table I.

5.3 Methods of Treatment

In accordance with the invention, there are provided methods of using the compounds of Formula I. The compounds used in the invention may be used to inhibit the degradation of sEH substrates having beneficial effects and/or inhibit the formation of metabolites that have adverse effects. The methods of the invention may be used to treat a variety of diseases related to dysfunction of vasodilation, inflammation, and/or endothelial cells. For example, the methods of the invention are useful for the treatment of conditions including, but not limited to, hypertension, such as primary or secondary hypertension, ischemic conditions such as angina, myocardial infarction, transient ischemic neurologic attack, cerebral ischemia, ischemic cerebral infarction, bowel infarction, etc. Additionally, inflammatory conditions including, but not limited to, type I hypersensitivity, atopy, anaphylaxis, asthma, osteoarthritis, rheumatoid arthritis, septic arthritis, gout, juvenile idiopathic arthritis, still's disease, ankylosing spondylitis, inflammatory bowel disease, Crohn's disease or inflammation associated with vertebral disc herniation may be treated according to the methods of the present invention. The invention may also be used to reduce the risk of ischemic damage to tissue associated with atherosclerosis.

According to the invention, a "subject" or "patient" is a human or non-human animal. Although the animal subject is preferably a human, the compounds and compositions of the invention have application in veterinary medicine as well, e.g., for the treatment of domesticated species such as canine, feline, and various other pets; farm animal species such as bovine, equine, ovine, caprine, porcine, etc.; wild animals, e.g., in the wild or in a zoological garden; and avian species, such as chickens, turkeys, quail, songbirds, etc.

In one embodiment, the subject or patient has been diagnosed with, or has been identified as having an increased risk of developing, a disease related to dysfunction of vasodilation, inflammation, and/or an endothelial cell dysfunction.

In other non-limiting embodiments, the present invention provides for methods of reducing the risk of damage resulting from diseases related to dysfunction of vasodilation, inflammation, and/or endothelial cell dysfunction to a tissue of a subject comprising administering to the subject, an effective amount of a composition according to the invention.

The present invention provides for methods of treating diseases related to dysfunction of vasodilation, inflammation, and/or endothelial cell dysfunction in a subject in need of such treatment by administration of a therapeutic formulation which comprises a compound of Formula I. In particular embodiments, the formulation may be administered to a subject in need of such treatment in an amount effective to inhibit sEH enzymatic activity. Where the formulation is to be administered to a subject in vivo, the formulation may be administered systemically (e.g. by intravenous injection, oral administration, inhalation, etc.), or may be administered by any other means known in the art. The amount of the formulation to be administered may be determined using methods known in the art, for example, by performing dose response studies in one or more model system, followed by approved clinical testing in humans.

In another non-limiting embodiment of the invention, a subject to be treated with a compound of Formula I suffers from metabolic syndrome, wherein administering a compound of Formula I to the subject reduces the subject's risk of developing coronary heart disease, type 2 diabetes and other diseases related to plaque buildups in artery walls, such as, for example, atherosclerosis, stroke and peripheral vascular disease.

In another non-limiting embodiment, the invention provides a method for inhibiting the activity of a soluble epoxide hydrolase which comprises contacting the soluble epoxide hydrolase with a compound of Formula I in an amount effective to inhibit soluble epoxide hydrolase activity.

In other non-limiting embodiments, the invention provides a method for treating a disease related to dysfunction of vasodilation, inflammation, and/or endothelial cell dysfunction in an individual, which method comprises administering to the individual an effective amount of a compound according to Formula I.

Figure 5:
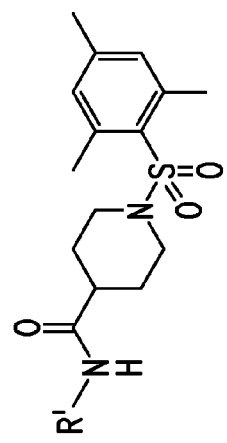
FIG. 5 Shows compounds and their biological results for the head (i.e. $R^1$) modifications of compound 1.

In certain non-limiting embodiments of the invention, an effective amount of compound is an amount which results in a blood level of compound which is at least 20% or at least 50% or at least 90% of the $IC_{50}$. Non-limiting specific examples of compounds of the invention and their $IC_{50}$ values are shown in FIGS. 4 and 5.

According to the invention, an effective amount is an amount of a compound of Formula I which reduces the clinical symptoms of diseases related to dysfunction of vasodilation, inflammation, and/or endothelial cells. For example, an effective amount is an amount of a compound of Formula I that reduces abnormally high arterial blood pressure (for example but not by way of limitation, abnormally high systolic pressure, diastolic pressure, or both, wherein systolic blood pressure is at least 140 mm Hg and a diastolic blood pressure is at least 90 mm Hg), or inflammation in a subject, or increases the flow of blood to an organ or tissue, for example but not by way of limitation, the heart or brain in a subject.

In a further non-limiting embodiment, the effective amount of a compound of Formula I may be determined via an in vitro assay. By way of example, and not of limitation, such an assay may utilize an sEH enzyme and a substrate which can report the level of sEH activity through a detectable signal, such as, for example, a change in luminescence, coloration, temperature, or fluorescence. In one embodiment, the assay is a high throughput fluorescent assay that utilizes a recombinant human sEH and a water soluble α-cyanocarobonate epoxide (PHOME) substrate (see, e.g., Wolf et al., 2006, Anal. Biochem 335:71-80). According to the invention, the assay can be initiated by sEH-catalyzed hydrolysis of the non-fluorescent PHOME substrate followed by spontaneous cyclization to give a cyanohydrin. Under basic condition, the cyanohydrin rapidly decomposes into a highly fluorescent product. Fluorescence with excitation at 320 nm and emission at 460 nm can be recorded at the endpoint of the reaction cascade with or without the presence of assay samples. When the hydrolysis reaction is performed in the presence of a compound of Formula I, a decrease in recorded fluorescence indicates inhibition of sEH enzymatic activity, wherein a greater decrease in fluorescence indicates a greater inhibition of sEH.

In one non-limiting embodiment, an effective amount of a compound of Formula I may be an amount that results in a local concentration of compound at the therapeutic site (such as, but not limited to, the serum concentration) of from at least about 0.01 nM to about 2 μM, preferably from at least about 0.01 nM to about 200 nM, and more preferably from at least about 0.01 nM to about 50 nM.

In another non-limiting embodiment, an effective amount of a compound of Formula I may be correlated with the compound's ability to inhibit sEH activity by at least about 5-10%, more preferably from at least about 10-20%, more preferably from at least about 20-30%, more preferably from at least about 30-40%, more preferably from at least about 40-50%, more preferably from at least about 50-60%, more preferably from at least about 60-70%, more preferably from at least about 70-80%, more preferably from at least about 80-90%, and more preferably from at least about 90-100%, when the compound is administered in the in vitro assay, wherein a greater level of sEH inhibition at a lower concentration in the in vitro assay is correlative with the compound's therapeutic efficacy.

In a further non-limiting embodiment, the compound is administered at a concentration of 200 nM in the in vitro assay.

In a preferred non-limiting embodiment, an effective amount of a compound of Formula I may be correlated with the compound's ability to inhibit sEH activity by about at least 60% when the compound is administered at a concentration of 200 nM in the in vitro assay.

In other preferred non-limiting embodiments, an effective amount of a compound of Formula I may be correlated with the compound's ability to inhibit sEH activity by about at least 70% when the compound is administered at a concentration of 200 nM in the in vitro assay.

In other preferred non-limiting embodiments, an effective amount of a compound of Formula I may be correlated with the compound's ability to inhibit sEH activity by about at least 80% when the compound is administered at a concentration of 200 nM in the in vitro assay.

In other preferred non-limiting embodiments, an effective amount of a compound of Formula I may be correlated with the compound's ability to inhibit sEH activity by about at least 90% when the compound is administered at a concentration of 200 nM in the in vitro assay.

In other preferred non-limiting embodiments, an effective amount of a compound of Formula I may be correlated with the compound's ability to inhibit sEH activity by about at least 95% when the compound is administered at a concentration of 200 nM in the in vitro assay.

In other preferred non-limiting embodiments, an effective amount of a compound of Formula I may be correlated with the compound's ability to inhibit sEH activity by about 100% when the compound is administered at a concentration of 200 nM in the in vitro assay.

In another non-limiting embodiment, an effective amount of a compound of Formula I may be correlated with the compound's ability to inhibit sEH activity by at least about 50% compared to a control cell line that was not contacted with the candidate compound (i.e., $IC_{50}$), wherein the compound is tested at a concentration ranging from at least about 200 nM to about 0.01 nM, preferably from at least about 100 nM to about 0.01 nM, and more preferably from at least about 10 nM to about 0.01 nM in the in vitro assay, wherein such inhibition of sEH activity at the above-described concentrations is correlative with the compound's therapeutic efficacy.

In other non-limiting embodiments, an effective amount of a compound of Formula I may be correlated with the compound's ability to inhibit sEH activity by about at least 50% when the compound is administered at a concentration of about 90 nM in the in vitro assay.

In other non-limiting embodiments, an effective amount of a compound of Formula I may be correlated with the compound's ability to inhibit sEH activity by about at least 50% when the compound is administered at a concentration of 80 nM in the in vitro assay.

In other non-limiting embodiments, an effective amount of a compound of Formula I may be correlated with the compound's ability to inhibit sEH activity by about at least 50% when the compound is administered at a concentration of about 40 nM in the in vitro assay.

In other non-limiting embodiments, an effective amount of a compound of Formula I may be correlated with the compound's ability to inhibit sEH activity by about at least 50% when the compound is administered at a concentration of about 20 nM in the in vitro assay.

In other non-limiting embodiments, an effective amount of a compound of Formula I may be correlated with the compound's ability to inhibit sEH activity by about at least 50% when the compound is administered at a concentration of about 10 nM in the in vitro assay.

In other non-limiting embodiments, an effective amount of a compound of Formula I may be correlated with the compound's ability to inhibit or reduce inflammation or pain, for example, mechanical allodynia or thermal hyperalgesia, in vivo, wherein a greater reduction in inflammation or pain at a lower concentration compared to a control subject that is not administered the compound is correlative with the compound's therapeutic efficacy. By way of example, and not of limitation, such an in vivo assay may comprise administering a compound of Formula I to a test subject, for example, a mouse or rat, followed by an assay to determine a change in inflammation or pain in the subject. The assay used to measure inflammation or pain may be any assay known in the art, for example, behavioral assays such as an electronic Von Frey test, tail flick assay or thermal paw withdrawal test.

In one embodiment, inflammation or pain may be induced in the subject using methods known in the art, such as, for example, by administering Complete Freund's Adjuvant (CFA) to the test subject. The inflammation or pain may be induced prior to, at the same time as, or after administration of the compound of Formula I. When inflammation or pain is induced before the administration of a compound of Formula I, the inflammation or pain may be induced at least 5 minutes, at least 30 minutes, at least 1 hour, at least 5 hours, at least 10 hours, at least 24 hours, at least 2 days, at least 5 days, or at least 1 week or more before the compound of formula I is administered. The level of inflammation or pain in the test subject may be assayed following induction.

In another embodiment of the invention, the level of inflammation or pain in the test subject may be assayed before inflammation or pain is induced. Inflammation or pain may be assayed again when the compound of formula I is administered, and at intervals following administration of the compound, for example, at intervals of at least 5 seconds, at least 10 seconds, at least 30 seconds, at least 1 minute, at least 5 minutes, at least 30 minutes, at least 1 hour, at least 5 hours, at least 10 hours, at least 24 hours, at least 2 days, at least 5 days, or at least 1 week, or combinations thereof, following administration of the compound.

According to the invention, the component or components of a pharmaceutical composition of the invention may be introduced by intravenous, intra-arteriole, intramuscular, intradermal, transdermal, subcutaneous, oral, intraperitoneal, intraventricular, and intrathecal administration.

In yet another embodiment, the therapeutic compound can be delivered in a controlled or sustained release system. For example, a compound or composition may be administered using intravenous infusion, an implantable osmotic pump, a transdermal patch, liposomes, or other modes of administration. In one embodiment, a pump may be used (see Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Langer and Wise eds., 1974, Medical Applications of Controlled Release, CRC Press: Boca Raton, Fla.; Smolen and Ball eds., 1984, Controlled Drug Bioavailability, Drug Product Design and Performance, Wiley, N.Y.; Ranger and Peppas, 1983, J. Macromol. Sci. Rev. Macromol. Chem., 23:61; Levy et al., 1985, Science 228:190; During et al., 1989, Ann. Neurol., 25:351; Howard et al., 9189, J. Neurosurg. 71:105). In yet another embodiment, a controlled release system can be placed in proximity of the therapeutic target, i.e., the heart or a blood vessel, thus requiring only a fraction of the systemic dose (see, e.g., Goodson, 1984, in Medical Applications of Controlled Release, supra, Vol. 2, pp. 115-138). Other controlled release systems known in the art may also be used.

5.4 Pharmaceutical Compositions

The compounds and compositions of the invention may be formulated as pharmaceutical compositions by admixture with a pharmaceutically acceptable carrier or excipient.

In one non-limiting embodiment, the pharmaceutical composition may comprise an effective amount of a compound of Formula I and a physiologically acceptable diluent or carrier. The pharmaceutical composition may further comprise a second drug, for example, but not by way of limitation, an anti-hypertension drug or an anti-inflammatory drug.

The phrase "pharmaceutically acceptable" refers to molecular entities and compositions that are physiologically tolerable when administered to a subject. Preferably, but not by way of limitation, as used herein, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, or, for solid dosage forms, may be standard tabletting excipients. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin, 18th Edition, or other editions.

In a specific embodiment, the therapeutic compound can be delivered in a vesicle, in particular a liposome (see Langer, 1990, Science 249:1527-1533; Treat et al., 1989, in Liposomes in the Therapy of Infectious Disease and Cancer, Lopez-Berestein and Fidler eds., Liss: New York, pp. 353-365; Lopez-Berestein, ibid., pp. 317-327; see generally Lopez-Berestein, ibid.).

EXAMPLES

Example 1

Screening Assay to Identify Inhibitors of sEH

Figure 1:
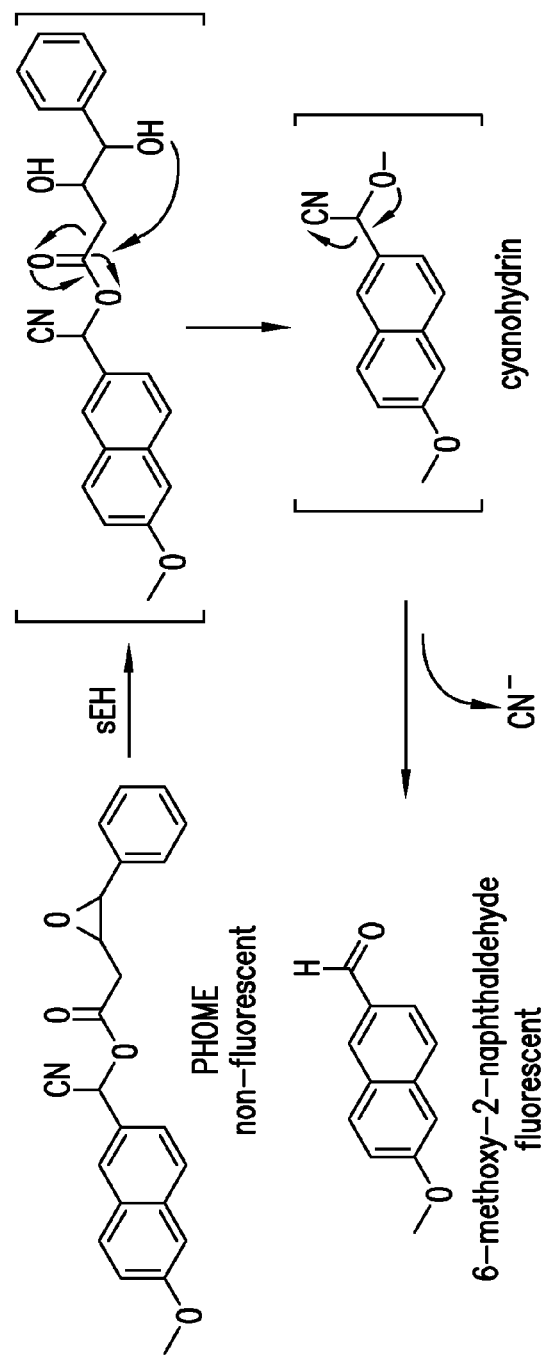
FIG. 1 Shows a reaction mechanism of a fluorescent high throughput screen encompassed by the present invention. In the screen, the sEH substrate PHOME fluoresces following sEH-catalyzed hydrolysis.

A fluorescent assay was employed for high throughput screening (HTS) of inhibitors of she. This HTS employs recombinant human sEH and a water soluble α-cyanocarobonate epoxide (PHOME) as the substrate (Wolf et. al. Anal Biochem. 2006, 335, 71). As shown in FIG. 1, the assay was initiated by sEH-catalyzed hydrolysis of the non-fluorescent substrate followed by spontaneous cyclization to give a cyanohydrin. Under basic condition, the cyanohydrin rapidly decomposed into a highly fluorescent product. Fluorescence with excitation at 320 nm and emission at 460 nm was recorded at the endpoint of the reaction cascade with or without the presence of assay samples.

Figure 2:
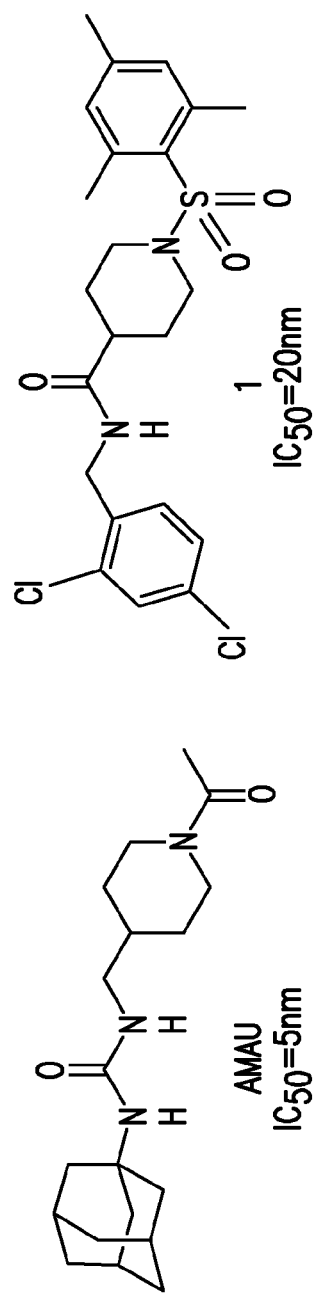
FIG. 2 Shows the structure of sEH inhibitors AMAU and sulfonyl isonipecotamide (compound 1).

From a compound collection provided by the NIH Roadmap project, a variety of hits were identified having low micromolar to nanomolar potency (See the screen results published in Pubchem [AID:1026]). Several non-urea compounds exhibited therapeutically acceptable activities in this screening. Among these, sulfonyl isonipecotamide 1 (FIG. 2), a nanomolar inhibitor ($IC_{50}$=20.0 nm) structurally similar to previously reported piperidine-based sEH inhibitors such as AMAU (FIG. 2), was of particular interest (Jones et al. Bioorg Med Chem. Lett. 2006, 16, 5212).

Figure 3:
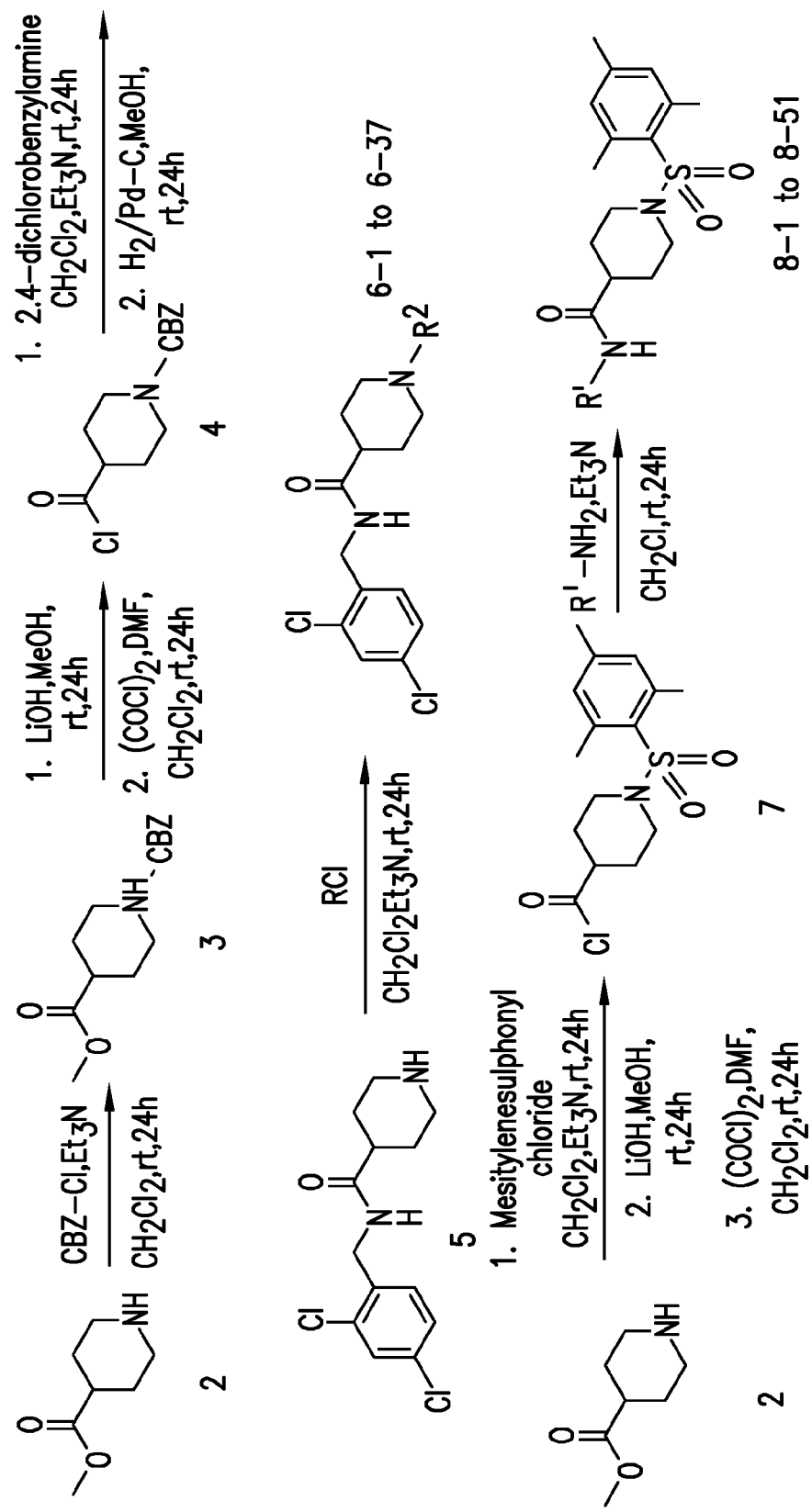
FIG. 3 Shows the synthesis of compound 6-1 to 6-37 and compound 8-1 to 8-51

To identify alternative inhibitory compounds, a secondary library was rapidly assembled by modifying the amide head group and the sulfonamide tail group of 1. The design strategy was to keep one group in tact while modifying the other, in an attempt to identify a "super" compound generated from a combination of the best head and tail. The synthesis is outlined in FIG. 3. Methyl isonipecotate 2 (FIG. 3) was first protected with benzyl chloroformate, and then converted into acid chloride 4 (FIG. 3) by removing the methyl ester and treating with oxalyl chloride. Coupling of 4 with 2,4-dichlorobenzylamine followed by Palladium catalyzed hydrogenation afforded amine 5 (FIG. 3), which reacted with a variety of sulfonyl chlorides, acid chlorides and chloroformates to give the final products 6-1 to 6-36. On the other hand, 2 was treated with mesitylenesulphonyl chloride and similarly converted into acid chloride 7 (FIG. 3). In parallel, reaction of 7 with various amines led to the target compounds 8-1 to 8-50.

New compounds were first screened at concentrations of 2 μM, 400 nm and 200 nm using the fluorescence assay described above. The $IC_{50}$s were further determined for those compounds showing more than 50% inhibition at the concentration of 200 nm. The biological results for the tail and head modification are summarized in FIG. 4 and FIG. 5, respectively.

As illustrated in FIG. 4, the diverse tail modification did not improve inhibitory potency over the mesitylenesulfonamide identified from the original screen (i.e. compound 1). However, several structure activity relationships were observed in this series. First, the functionality of sulfonamide is important for potent inhibition. Great loss of activities was observed for amides (6-26, 6-27 and 6-29) compared with the corresponding sulfonamides. Aromatic sulfonamides appear to be more favorable as all tested alkylsulfonamides are poor inhibitors. Substitution on the aromatic ring can further affect the activities. Hydrophobic alkyl groups and halides are generally preferred. Interestingly, their positive effect is more pronounced at ortho position. For example, a bromide or fluoride at ortho position (6-6, 6-10) confers nanomolar potency but not at para position (6-19). Deleting the ortho methyl groups in 1 led to less active compounds 6-1 and 6-24.

In the optimization of the head group, a set of structurally diversified amides were first screened. All disubstituted amides tested were inactive (results not shown), suggesting the proton in NH is essential to sEH inhibition. Previous studies with urea-based inhibitors have shown that one NH of the urea, which forms a salt bridge with the catalytic nucleophile $Asp^{333}$ in the active side of sEH, is required for inhibitory activity (Argiriadi et al., J Biol. Chem. 2000, 275(20), 15265). It becomes apparent that the amide in positive hit corresponds to the urea functionality serving as the primary pharmacophore. A variety of primary amines were selected to replace 2,4-dichloride benzylamine moiety, including those frequently found in urea inhibitors. As shown in FIG. 5, the amide is quite tolerant to modification and nanomolar potency is retained with various scaffolds. N-benzylamide 8-9 ($IC_{50}$=42.0 nm) and N-cyclohexylamide 8-14, ($IC_{50}$=16.4 nm) represent favorable choices for further optimization. Exhaustively adjusting the benzyl group led to improved potency in 8-37 ($IC_{50}$=12.7 nm). The most noticeable SAR illustrated by this modification is that halides such as chloride and Fluoride seem favored for the substitutions of the benzyl group. Modification of cyclohexylamide was successful and resulted in several inhibitors with a potency that achieved a single digital nanomolar range. As demonstrated by compounds 8-42 ($IC_{50}$=7.9 nm) and 8-47 ($IC_{50}$=12.6 nm), wherein an extra methylene added to the cyclohexyl ring enhanced inhibitory activity. In contrast, polar atoms (N, O) in the ring reduce inhibition to the micromolar range (8-49, 8-50). These SARs are consistent with previous results obtained for urea derivatives (Kim et al. J Med. Chem. 2005, 48, 3621).

In summary, a series of potent non-urea sEH inhibitors have been successfully identified via high throughput screens. Improved potency was sought through SAR-guided modification. The compound 8-42 with an $IC_{50}$ of 7.9 nm represents the most potent non-urea sEH inhibitor identified in this study.

Example 2

In Vivo Effect of sEH Inhibitors on Mechanical Allodynia and Thermal Hyperalgesia The effectiveness of a compound of Formula I in reducing pain sensitivity was examined in vivo. Inflammation was induced by injection of Complete Freund's Adjuvant (CFA) into the footpad of six mice at day 1 of the study. 24 hours following CFA administration, two test animals received a subcutaneous injection of compound 8-42. Compound 8-42 was dissolved in 100% DMSO prior to administration. As a positive control, an analgesic effect was elicited in one animal by administering the Protein Kinase G (PKG) inhibitor RPG (exemplary RPGs include Rp-cGMPs) intrathecally 24 hours after CFA administration. As a negative control, one animal was administered an intrathecal injection of saline and a subcutaneous injection of 100% DMSO 24 hours after CFA. Additionally, two animals were administered a subcutaneous injection of compound 8-42 and an intrathecal injection of RPG 24 hours after CFA to determine if the two compounds could achieve an additive or synergistic analgesic effect.

Pain sensitivity was measured using two behavioral assays. The electronic Von Frey test was used to measure mechanical allodynia in the control and test animals, while the thermal paw withdrawal test was used to measure thermal hyperalgesia. The electronic Von Frey test consisted of application of a filament against the rodent's paw, whereby paw withdrawal caused by the stimulation is registered as a response. The corresponding force (resistance) applied was recorded in grams. The thermal paw withdrawal test comprised applying a thermal stimulus to the rodent's foot, whereby the withdrawal latency was measured as a response.

A baseline sensitivity to pain was first measure prior to CFA treatment, and again after administration of CFA. Pain sensitivity was then assayed 24 hours later at day 2 following the administration of compound 8-42 or the control agents, and again at day 5. As shown in FIG. 6, 8-42 did not reduce CFA-induced mechanical allodynia or thermal hyperalgesia compared to RPG and the control agents. Furthermore, the combination of 8-42 and RPG did not produce an additive or synergistic reduction in CFA-induced mechanical allodynia or thermal hyperalgesia compared to RPG or 8-42 treatment alone.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, product descriptions, GenBank Accession Numbers, and protocols are cited throughout this application, the disclosures of which are incorporated herein by reference in their entireties for all purpose.

What is claimed is:
1. A compound of Formula I:

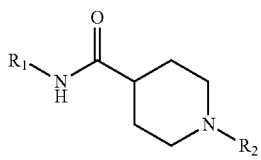

wherein $R^1$ is independently selected for each occurrence from the group consisting of

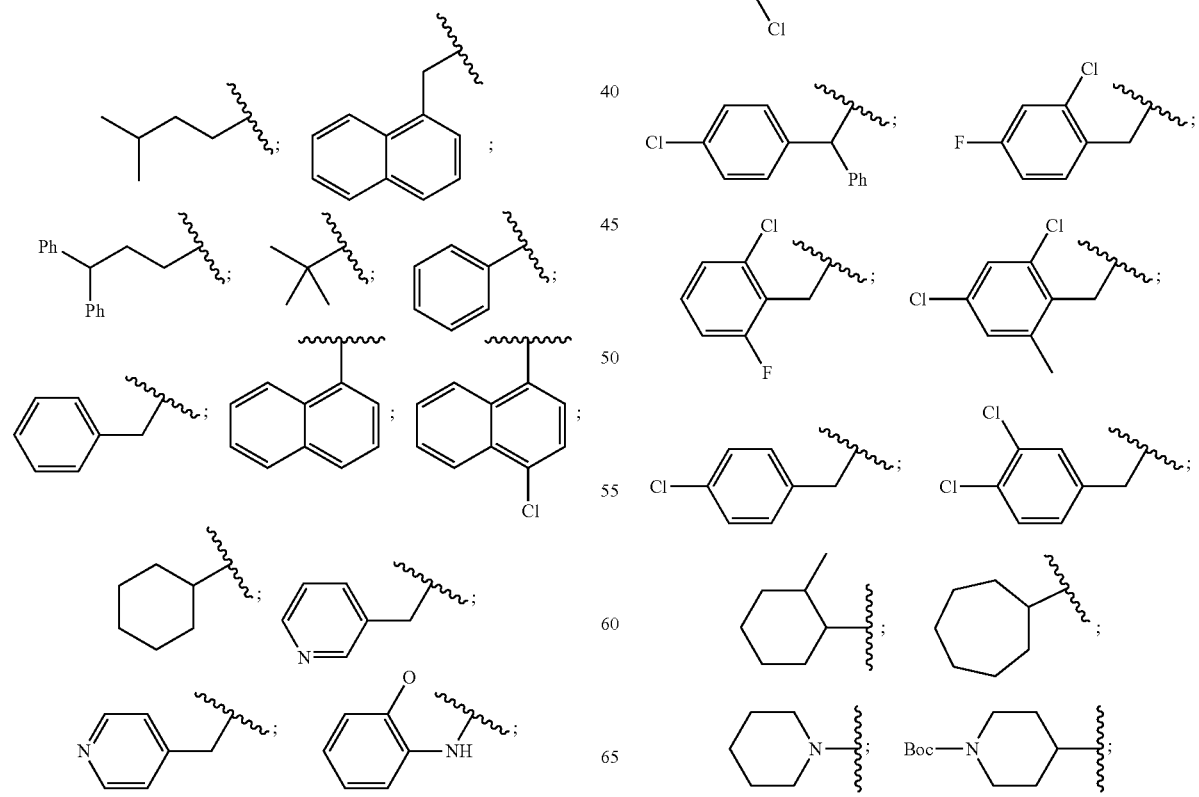

-continued
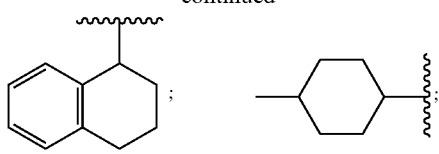
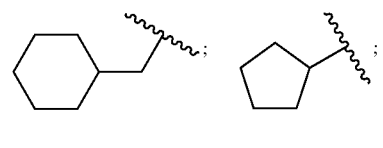
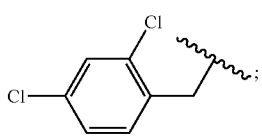
wherein R² is independently selected for each occurrence from the group consisting of
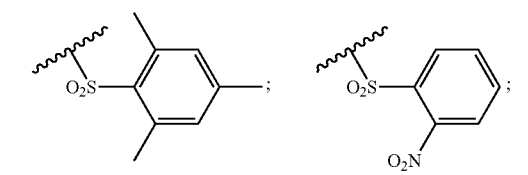
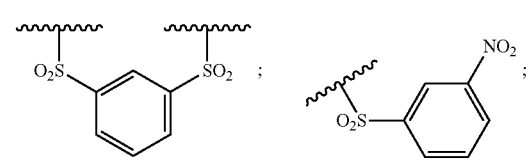
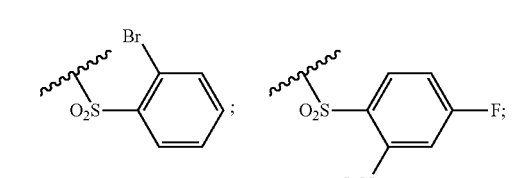
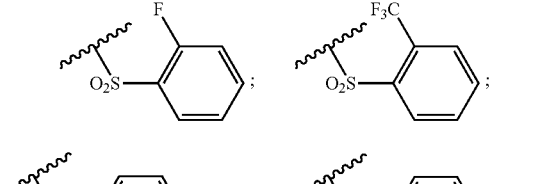
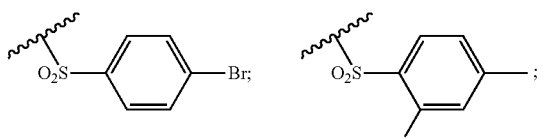
-continued
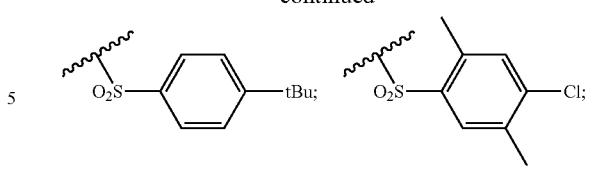
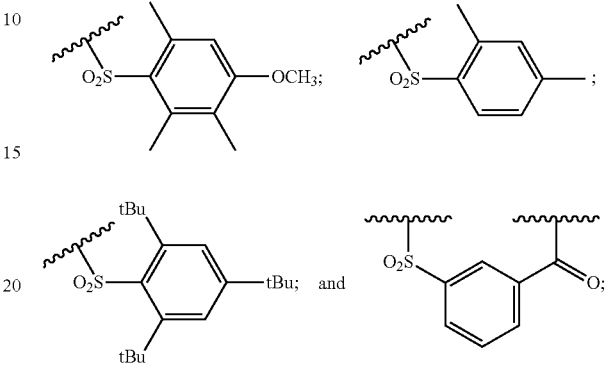
and further wherein, when R² is
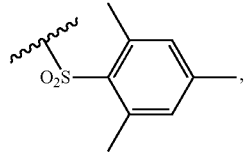 [SMILES: *S(=O)(=O)c1c(C)cc(C)cc1C]
R¹ is not
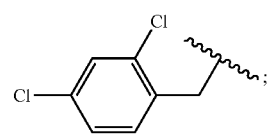 [SMILES: *Cc1ccc(Cl)cc1Cl]
and pharmaceutically acceptable salts thereof.
2. The compound of claim 1, wherein R² is selected from the group consisting of
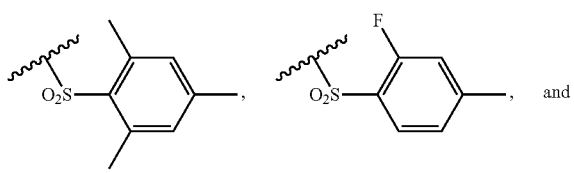
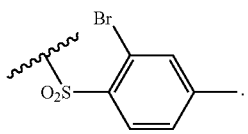
3. The compound of claim 1, wherein R¹ is selected from the group consisting of:

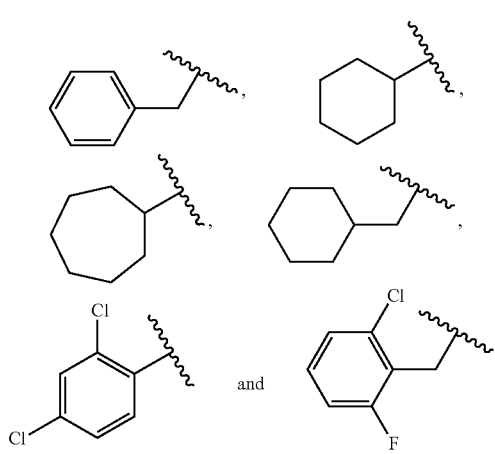

and

4. The compound of claim 1, wherein the compound is:

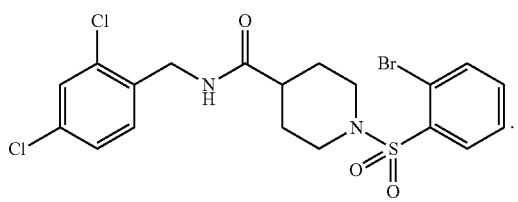

5. The compound of claim 1, wherein the compound is:

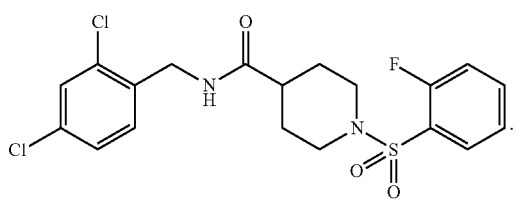 [SMILES: O=C(NCc1ccc(Cl)cc1Cl)C1CCN(S(=O)(=O)c2ccccc2Br)CC1]

6. The compound of claim 1, wherein the compound is:

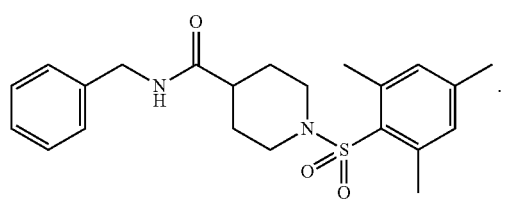 [SMILES: Cc1cc(C)c(S(=O)(=O)N2CCC(C(=O)NCc3ccccc3)CC2)c(C)c1]

7. The compound of claim 1, wherein the compound is:

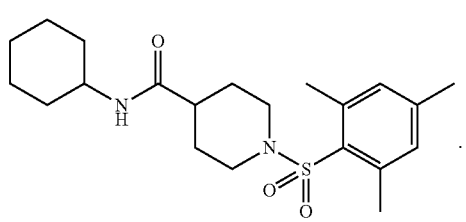 [SMILES: Cc1cc(C)c(S(=O)(=O)N2CCC(C(=O)NC3CCCCC3)CC2)c(C)c1]

8. The compound of claim 1, wherein the compound is:

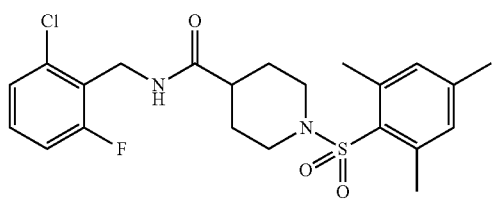

9. The compound of claim 1, wherein the compound is:

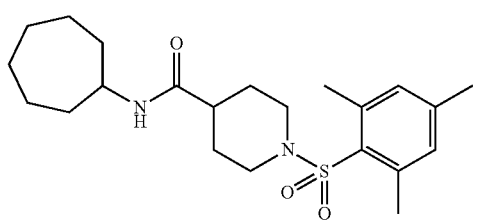

10. The compound of claim 1, wherein the compound is:

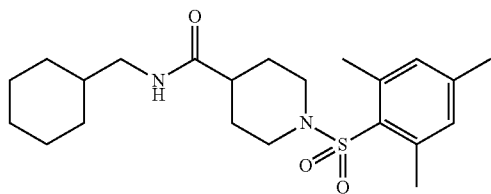

11. A pharmaceutical formulation comprising a compound of Formula I,

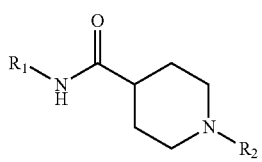

wherein $R^1$ is independently selected for each occurrence from the group consisting of

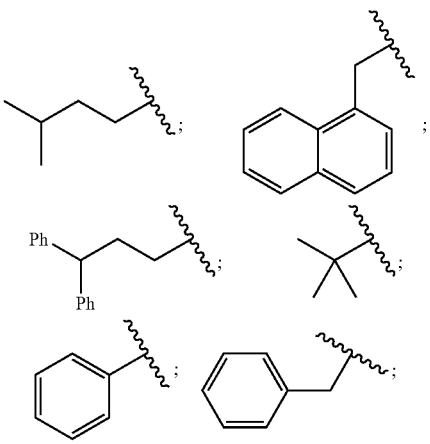

wherein R² is independently selected for each occurrence from the group consisting of -continued
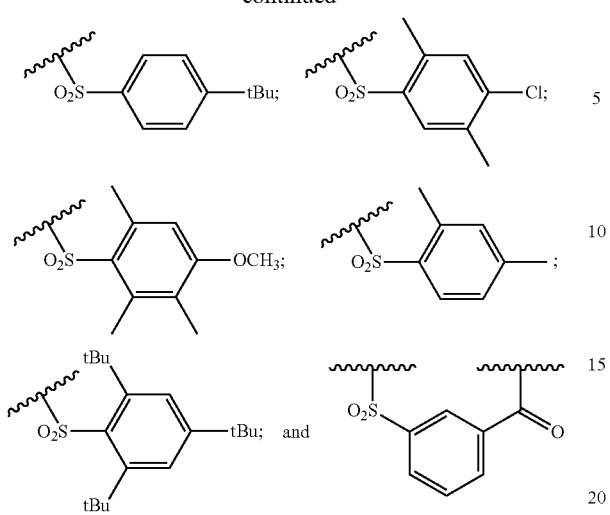
and further wherein, when $R^2$ is
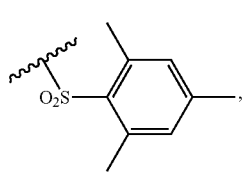 [SMILES: *S(=O)(=O)c1c(C)cc(C)cc1C]
$R^1$ is not
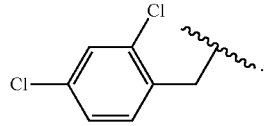 [SMILES: *Cc1ccc(Cl)cc1Cl]
12. A compound of Formula VII:
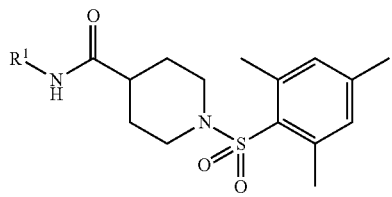
wherein $R^1$ is selected from the group consisting of
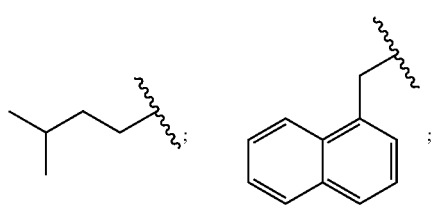
-continued
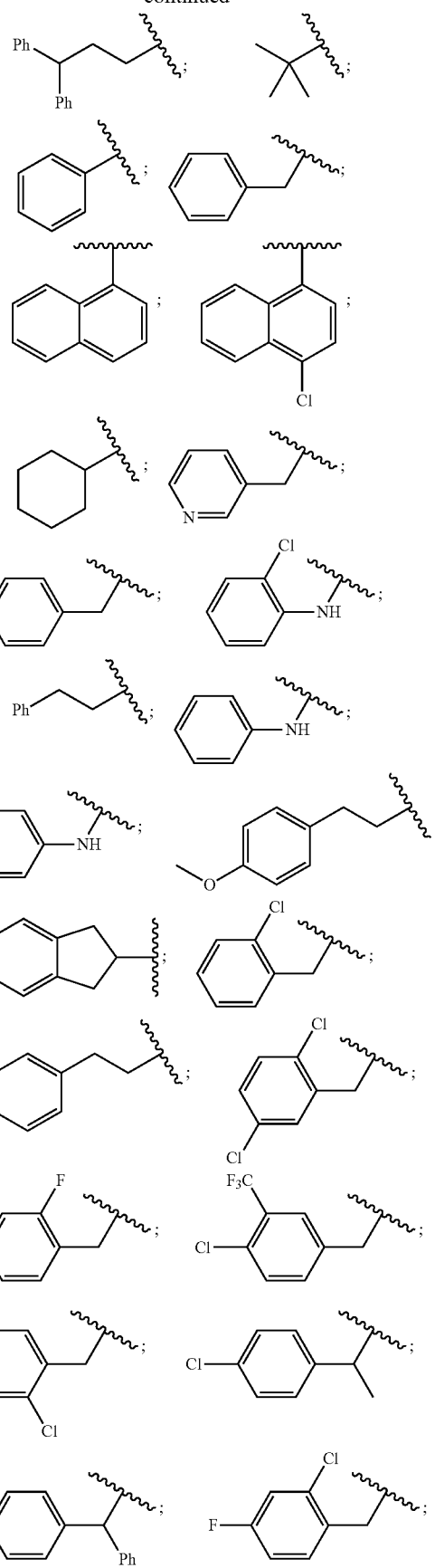

-continued
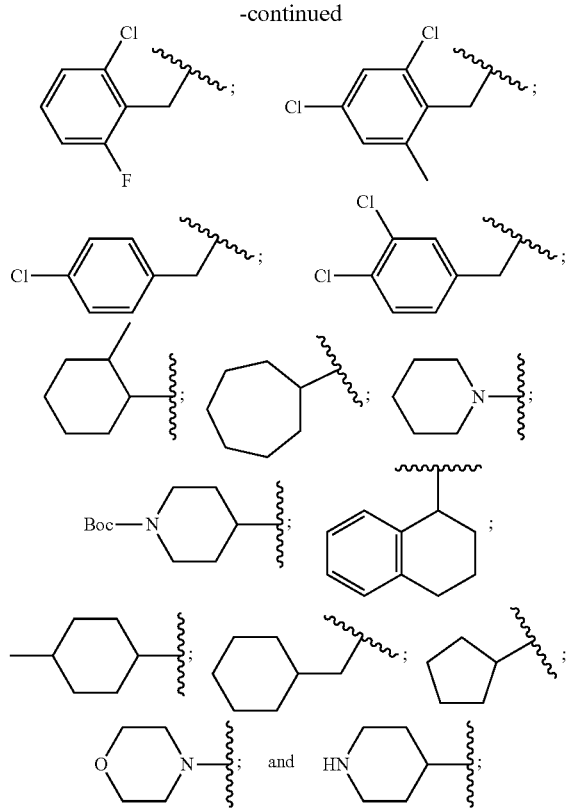
and pharmaceutically acceptable salts thereof.
13. A compound of Formula VIII:
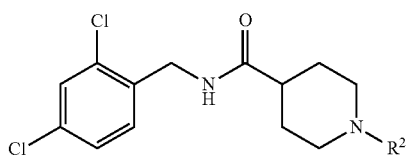
wherein R² is selected from the group consisting of
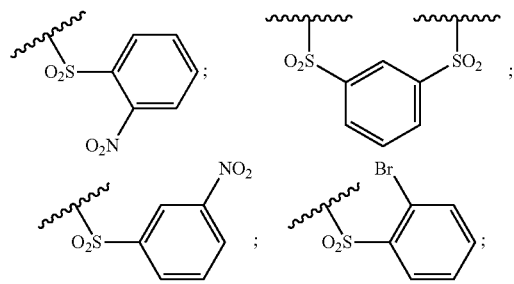
-continued
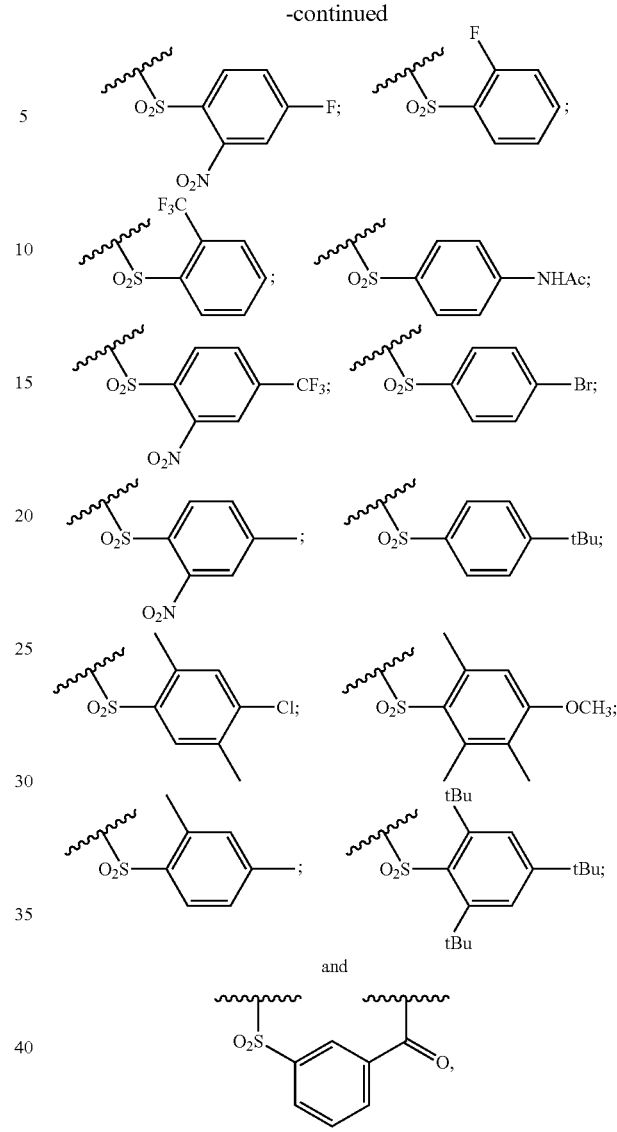
and pharmaceutically acceptable salts thereof.
14. The compound of claim 1, wherein the compound is:
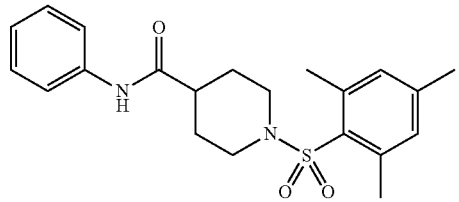
* * * * *